(12) United States Patent
Wu

(10) Patent No.: US 11,420,942 B2
(45) Date of Patent: Aug. 23, 2022

(54) CRYSTALLINE FORMS OF [3-(4-{2-BUTYL-1-[4-(4-CHLORO-PHENOXY)-PHENYL]-1H-IMIDAZOL-4-YL}-PHENOXY)-PROPYL]-DIETHYL-AMINE

(71) Applicant: vTv Therapeutics LLC, High Point, NC (US)

(72) Inventor: Zheqiong Wu, Princeton, NJ (US)

(73) Assignee: VTV THERAPEUTICS LLC, High Point, NC (US)

( * ) Notice: Subject to any disclaimer, the term of this patent is extended or adjusted under 35 U.S.C. 154(b) by 0 days.

(21) Appl. No.: 17/019,586

(22) Filed: Sep. 14, 2020

(65) Prior Publication Data

US 2021/0070714 A1 Mar. 11, 2021

Related U.S. Application Data

(63) Continuation of application No. PCT/US2019/022932, filed on Mar. 19, 2019.

(60) Provisional application No. 62/649,161, filed on Mar. 28, 2018.

(51) Int. Cl.
*C07D 233/60* (2006.01)
*A61K 31/4164* (2006.01)

(52) U.S. Cl.
CPC ........ *C07D 233/60* (2013.01); *C07B 2200/13* (2013.01)

(58) Field of Classification Search
CPC .......................... C07D 233/60; A61K 31/4164
USPC ........................................ 548/336.1; 514/400
See application file for complete search history.

(56) References Cited

U.S. PATENT DOCUMENTS

| | | | |
|---|---|---|---|
| 4,265,874 A | 5/1981 | Bonsen et al. | |
| 4,356,108 A | 10/1982 | Schwab et al. | |
| 5,011,849 A | 4/1991 | Gassner et al. | |
| 5,166,214 A | 11/1992 | Billheimer et al. | |
| 5,550,833 A | 8/1996 | Fujisawa | |
| 5,585,344 A | 12/1996 | Vlassara et al. | |
| 5,817,826 A | 10/1998 | Ohtani et al. | |
| 5,840,294 A | 11/1998 | Kisilevsky et al. | |
| 5,864,018 A | 1/1999 | Morser et al. | |
| 5,922,770 A | 7/1999 | Peschke et al. | |
| 5,939,526 A | 8/1999 | Gaugler et al. | |
| 5,962,535 A | 10/1999 | Miyamoto et al. | |
| 6,221,887 B1 | 4/2001 | Asghar et al. | |
| 6,268,479 B1 | 7/2001 | Stern et al. | |
| 6,323,218 B1 | 11/2001 | Bush et al. | |
| 6,441,049 B2 | 8/2002 | Reitz et al. | |
| 6,613,801 B2 | 9/2003 | Mjalli et al. | |
| 6,677,299 B2 | 1/2004 | Stern et al. | |
| 6,825,184 B2 | 11/2004 | Cirillo et al. | |
| 7,067,554 B2 | 6/2006 | Mjalli et al. | |
| 7,087,832 B2 | 8/2006 | Scher et al. | |
| 7,329,884 B2 | 2/2008 | Kondo et al. | |
| 7,361,678 B2 | 4/2008 | Mjalli et al. | |
| 7,381,678 B2 | 6/2008 | Filimonov et al. | |
| 7,421,177 B2 | 9/2008 | Schmid et al. | |
| 7,423,177 B2 | 9/2008 | Mjalli et al. | |
| 7,714,013 B2 | 5/2010 | Mjalli et al. | |
| 7,737,285 B2 | 6/2010 | Mjalli et al. | |
| 7,776,919 B2 | 8/2010 | Mjalli et al. | |
| 7,884,219 B2 * | 2/2011 | Hari ........................ | A61P 29/00 548/470 |
| 8,274,815 B2 | 9/2012 | Ichihara et al. | |
| 8,372,988 B2 | 2/2013 | Hari | |
| 8,472,145 B2 | 6/2013 | Ho et al. | |
| 9,717,710 B2 | 8/2017 | Orlandi et al. | |
| 2001/0039256 A1 | 11/2001 | Stern et al. | |
| 2002/0006957 A1 | 1/2002 | Mjalli et al. | |
| 2002/0118725 A1 | 8/2002 | Mollenkopf | |
| 2002/0122799 A1 | 9/2002 | Stern et al. | |
| 2002/0193432 A1 | 12/2002 | Mjalli et al. | |
| 2003/0032663 A1 | 2/2003 | M. Mjalli et al. | |
| 2004/0063770 A1 | 4/2004 | Ahn et al. | |
| 2004/0082542 A1 * | 4/2004 | Mjalli ..................... | A61P 17/00 514/63 |
| 2004/0097407 A1 | 5/2004 | Mjalli et al. | |
| 2005/0026811 A1 * | 2/2005 | Mjalli ..................... | A61P 43/00 514/365 |
| 2006/0020042 A1 | 1/2006 | McDonald et al. | |
| 2006/0247253 A1 | 11/2006 | Leban et al. | |
| 2007/0021386 A1 | 1/2007 | Mjalli et al. | |
| 2007/0135437 A1 | 6/2007 | Benjamin et al. | |
| 2009/0035302 A1 | 2/2009 | Mjalli et al. | |
| 2010/0048726 A1 | 2/2010 | Mcdonald et al. | |
| 2010/0256119 A1 | 10/2010 | Mjalli et al. | |
| 2012/0088778 A1 | 4/2012 | Mjalli et al. | |
| 2014/0039025 A1 | 2/2014 | Jones et al. | |

(Continued)

FOREIGN PATENT DOCUMENTS

WO  WO-9509838 A1  4/1995
WO  WO-9728913 A1  8/1997

(Continued)

OTHER PUBLICATIONS

Amendment No. 6 to Form S-1 Registration Statement for vTv Therapeutics Inc.. Jul. 24, 2015. pp. 2-3, 84, 96-99.
Aricepto package insert. Feb. 2012.
Barile et al. The RAGE Axis in Early Diabetic Retinopathy. Investigative Opththmology & Visual Science 46(8):2916-2924 (2005).
Basta et al. Advanced glycation end products and vascular inflammation: implications for accelerated atherosclerosis in diabetes. Cardiovascular Research 63:582-592 (2004).

(Continued)

*Primary Examiner* — Charanjit Aulakh
(74) *Attorney, Agent, or Firm* — Wilson Sonsini Goodrich & Rosati

(57) ABSTRACT

The present invention relates to crystalline forms of [3-(4-{2-butyl-1-[4-(4-chloro-phenoxy)-phenyl]-1H-imidazol-4-yl}-phenoxy)-propyl]-diethylamine ("COMPOUND I") useful in the treatment of RAGE mediated diseases.

17 Claims, 4 Drawing Sheets

(56) References Cited

U.S. PATENT DOCUMENTS

| | | | |
|---|---|---|---|
| 2017/0326113 | A1 | 11/2017 | Orlandi et al. |
| 2019/0142803 | A1 | 5/2019 | Orlandi et al. |

FOREIGN PATENT DOCUMENTS

| | | | |
|---|---|---|---|
| WO | WO-9739121 A1 | 10/1997 | |
| WO | WO-9739125 A1 | 10/1997 | |
| WO | WO-9822138 A1 | 5/1998 | |
| WO | WO-9904485 A1 | 1/1999 | |
| WO | WO-9907402 A1 | 2/1999 | |
| WO | WO-9918987 A1 | 4/1999 | |
| WO | WO-0019994 A1 | 4/2000 | |
| WO | WO-0020458 A1 | 4/2000 | |
| WO | WO-0020821 A1 | 4/2000 | |
| WO | WO-0112598 A2 | 2/2001 | |
| WO | WO-0192210 A1 | 12/2001 | |
| WO | WO-02070473 A2 | 9/2002 | |
| WO | WO-02089965 A1 | 11/2002 | |
| WO | WO-03075921 A2 | 9/2003 | |
| WO | WO-2004087653 A2 | 10/2004 | |
| WO | WO-2004110350 A2 | 12/2004 | |
| WO | WO-2005000295 A1 | 1/2005 | |
| WO | WO-2006124897 A2 | 11/2006 | |
| WO | WO-2008067121 A2 | 6/2008 | |
| WO | WO-2008123914 A1 | 10/2008 | |
| WO | WO-2008153957 A1 | 12/2008 | |
| WO | WO-2009107401 A1 | 9/2009 | |
| WO | WO-2010126745 A1 | 11/2010 | |
| WO | WO-2011103091 A1 | 8/2011 | |
| WO | WO-2014055588 A1 | 4/2014 | |
| WO | WO-2019190822 A1 | 10/2019 | |

OTHER PUBLICATIONS

Behl et al. Amyloid beta peptide induces necrosis rather than apoptosis. Brain Research 645:253-264 (1994).
Behl et al. Hydrogen Peroxide Mediates Amyloid beta Protein Toxicity. Cell 77:817-827 (1994).
Berge et al. Pharmaceutical Salts. Journal of Pharmaceutical Sciences 66(1):1-19 (Jan. 1977).
Bierhaus et al. Advanced Glycation End Product (AGE)-Mediated Induction of Tissue Factor in Cultured Endothelial Cells is Dependent on RAGE. Circulation 96:2262-2271 (1997).
Bishop et al. Neural mechanisms of ageing and cognitive decline. Nature 464:529-535 (2010).
Blacker et al. Reliability and Validity of NINCDS-ADRDA Criteria for Alzheimer's Disease. Arch. Neur. 51:1198-1204 (1994).
Bonetta. Door Slams on RAGE Alzheimer Research Forum Print News. Available at http://www.alzforum.org/new/detailprint.asp?id=2960 (Nov. 9, 2011).
Bonnardel-Phu et al. Acute Modulation of Albumin Microvascular Leakage by Advanced Glycation End Products in Microcirculation of Diabetic Rats In Vivo. Diabetes 48:2052-2058 (1999).
Burstein et al. Effect of TTP488 in patients with mild to moderate Alzheimer's disease. BMC Neurology 14:12 (2014).
Burstein et al. Development of Azeliragon, an Oral Small Molecule Antagonist of the Receptor for Advanced Glycation Endproducts, for the Potential Slowing of Loss of Cognition in Mild Alzheimer's Disease. J Prev Alzheimers Dis 5(2):149-154 (2018).
Burstein et al. Evaluation of the relationship between TTP488 plasma concentration and changes in ADAS-cog relative to placebo. Poster session presented at: the Alzheimer's Association International Conference. Jul. 13-18, 2013. Boston, Massachusetts.
Byrn et al. Pharmaceutical Solids: A Strategic Approach to Regulatory Considerations. Pharmaceutical Research 12(7):945-954 (1995).
Chartier-Harlin et al. Early-onset Alzheimer's disease caused by mutations at codon 717 of the beta-amyloid precursor protein gene. Nature 353:844-846 (1991).
Checler. Processing of the beta-Amyloid Precursor Protein and Its Regulation in Alzheimer's Disease. J Neurochemistry 65(4):1431-1444 (1995).

Chitaley et al. Antagonism of Rho-kinase stimulates rat penile erection via a nitric oxide-independent pathway. Nature Medicine 7(1):119-122 (2001).
Crall et al. The Extramural and Intramural Corollary Arteries in Juvenile Diabetes Mellitus. Am J Med 64:221-230 (1978).
Deane et al. RAGE mediates amyloid-beta peptide transport across the blood-brain barrier and accumulation in brain. Nature Medicine 9:907-913 (2003).
Degenhardt et al. Chemical modification of proteins by methylglyoxal. Cell Mol. Biol. 44:1139-1145 (1998).
Donahue et al. RAGE, LRP-1, and amyloid-beta protein in Alzheimer's disease. Ada Neuropathol 112:405-415 (2006).
Dyer et al. Accumulation of Maillard reaction products in skin collagen in diabetes and aging. J. Clin. Invest. 91:2463-2469 (1993).
Dyer et al. Formation of pentosidine during nonenzymatic browning of proteins by glucose. Identification of glucose and other carbohydrates as possible precursors of pentosidine in vivo. J. Biol. Chem. 266:11654-11660 (1991).
Fang et al. RAGE-dependent signing in microglia contributes to neuroinflammation, A-beta accumulation, and impaired teaming/memory in a mouse model of Alzheimer's disease. The FASEB J 24:1043-1055 (2010).
Galasko et al. A clinic trial of an inhibitor of RAGE-A-beta interactions in Alzheimer's disease. RI clinic trial manuscript. Aug. 8, 2012.
Galasko et al. Clinical-Neuropathologic Correlations in Alzheimer's Disease and Related Dementia. Arch. Neur. 51:888-895 (1994).
Galasko et al. Clinical trial of an inhibitor of RAGE-A-beta interactions in Alzheimer disease. Neurology 82:1536-1542 (2014).
Girouard et al. Neurovascular coupling in the normal brain and in hypertension, stroke, and Alzheimer disease. J. Appl. Physiol. 100:328-335 (2006).
Golub et al. Molecular Classification of Cancer: Class Discovery and Class Prediction by Gene Expression Monitoring. Science 286:531-537 (1999).
Goova et al. Blockade of Receptor for Advanced Glycation End-Products Restores Effective Wound Healing in Diabetic Mice. Am J Pathol 159:513-525 (2001).
Haass et al. Cellular Processing of beta-Amyloid Precursor Protein and the Genesis of Amyloid beta-Peptide. Cell 75:1039-1042 (1993).
Hambly et al. Reappraisal of the role of the diabetic state in coronary artery disease. Chest 70(2):251-257 (1976).
Hammes et al. Diabetic retinopathy risk correlates with intracellular concentrations of the glycoxidation product Nepsilon-(carboxymethyl) lysine independently of glycohaemoglobin concentrations. Diabetologia 42:603-607 (1999).
Hofmann et al. RAGE mediates a novel proinflammatory axis: a central cell surface receptor for S100/calgranulin polypeptides. Cell 97:889-901 (1999).
Hori et al. The receptor for advanced glycation end products (RAGE) is a cellular binding site for amphoterin. Mediation of neurite outgrowth and co-expression of rage and amphoterin in the developing nervous system. J. Biol. Chem. 270:25752-761 (1995).
Huttunen et al. Receptor for Advanced Glycation End Products (RAGE)-mediated Neurite Outgrowth and Activation of NF-kB Require the Cytoplasmic Domain of the Receptor but Different Downstream Signing Pathways. J Biol Chem 274(28):19919-19924 (1999).
Japanese Journal of Geriatrics 49(4):419-424 (2012).
Johnson et al. MDL 29311: Antioxidant With Marked Lipid- and Glucose-Lowering Activity in Diabetic Rats and Mice. Diabetes 42:1179-1186 (1993).
Kamboh. Molecular Genetics of Late-Onset Alzheimer's Disease. Annals of Human Genetics 68:381-404 (2004).
Kannel et al. Diabetes and Cardiovascular Disease: The Framingham Study. JAMA 241(19):2035-2038 (1979).
Kannel et al. Diabetes and Glucose Tolerance as Risk Factors for Cardiovascular Disease: The Framingham Study. Diabetes Care 2(2):120-126 (1979).
Kennedy et al. Familial Alzheimer's disease. Brain 116:309-324 (1993).
Kislinger et al. Receptor for Advanced Glycation End Products Mediates Inflammation and Enhanced Expression of Tissue Factor

(56) References Cited

OTHER PUBLICATIONS in Vasculature of Diabetic Apolipoprotein E-Null Mice. Arterioscler Thromb Vase Biol. 21:905-910 (2001).

Kostura et al. Efficacy of RAGE antagonist in murine model of Alzheimer's disease. Poster session presented at: the Alzheimer's Association International Congress: Jul. 13-18, 2014: Cophenhagen, Denmark.

Kostura et al. Novel Bach1 Modulators Increase HM0X1 and Suppress Hypertension in the Goldblatt Model of Renovascular Hypertension, American Heart Association Scientific Sessions, Nov. 2013, Poster.

Kumar et al. RAGE at the Blood-Brain Barrier Mediates Neurovascular Dysfunction Caused by Amyloid-bet-40 Peptide. Neurosci. Program, p. 141 #275.19 (2000).

Lander et al. Activation of the Receptor for Advanced Glycation End Products Triggers a p21(ras)-dependent Mitogen-activated Protein Kinase Pathway Regulated by Oxidant Stress. J Biol Chem 272(28):17810-17814 (1997).

Levy-Lahad et al. Candidate Gene for the Chromosome 1 Familial Alzheimer's Disease Locus, Science. New Series 269(5226):973-977 (1995).

Li et al. Characterization and functional analysis of the promoter of RAGE, the receptor for advanced glycation end products. J. Biol. Chem. 272:16498-16506 (1997).

Li et al. Sp1-binding elements in the promoter of RAGE are essential for amphoterin-mediated gene expression in cultured neuroblastoma cells. J. Biol. Chem. 273:30870-30878 (1998).

Mackic et al. Human blood-brain barrier receptors for Alzheimer's amyloid-beta 1-40. Asymmetrical binding, endocytosis, and transcytosis at the apical side of brain microvascular endothelial cell monolayer. J. Clin. Invest. 102:734-743 (1998).

Mangialasche. Alzheimer's disease: clinic tris and drug development. The LANCET Neurology 9(7):702-716 (2010).

McKhann et al. Clinical diagnosis of Alzheimer's disease: report of the NINCDS-ADRDA Work Group under the auspices of Department of Health and Human Services Task Force on Alzheimer's Disease. Neurology 34(7):939-944 (1984).

Miyata et al. beta 2-Microglobulin modified with advanced glycation end products is a major component of hemodialysis-associated amyloidosis. J. Clin. Invest. 92:1243-1252 (1993).

Miyata et al. The receptor for advanced glycation end products (RAGE) is a central mediator of the interaction of AGE-beta2microglobulin with human mononuclear phagocytes via an oxidant-sensitive pathway. Implications for the pathogenesis of dialysis-related amyloidosis J. Clin. Invest. 98:1088-1094 (1996).

Morcos et al. Activation of Tubular Epithelial Cells in Diabetic Nephropathy. Diabetes 51:3532-3544 (2002).

Morris et al. Place navigation impaired in rats with hippocampal lesions. Nature 297:681-683 (1982).

Namenda® package insert. Jan. 2007 2011.

Neeper et al. Cloning and expression of a cell surface receptor for advanced glycosylation end products of proteins. J. Biol. Chem. 267:14998-15004 (1992).

Ohkubo et al. Studies on Cerebral Protective Agents. VII. Synthesis of Novel 4-Arylazole Derivatives with Anti-anoxic Activity, Chem. Pharm. Bull. 43(6):947-954 (1995).

Oldfield et al. Advanced glycation end products cause epithelial-myofibroblast transdifferentiation via the receptor for advanced glycation end products (RAGE). J Clin Invest 108(12):1853-1863(2001).

Pappolla et al. The Heat Shock/Oxidative Stress Connection: Relevance to Alzheimer Disease. Mol Chem Neropathol 28:21-24 (1996).

Park et al. Suppression of accelerated diabetic atherosclerosis by the soluble receptor for advanced glycation endproducts. Nature Medicine 4(9):1025-1031 (1998).

Parkkinen et al. Amphoterin, the 30-kDa protein in a family of HMG1-type polypeptides. Enhanced expression in transformed cells, leading edge localization, and interactions with plasminogen activation. J. Biol. Chem. 268:19726-19738 (1993).

Pastor et al. Molecular Genetics of Alzheimer's Disease. Current Psychiatry Reports 6:125-133 (2004).

PCT/US2013/062964 International Search Report and Written Opinion dated Nov. 19, 2013.

PCT/US2019/022932 International Search Report and Written Opinion dated May 28, 2019.

Perrone et al. The Complexity of Sporadic Alzheimer's Disease Pathogenesis: The Role of RAGE as Therapeutic Target to Promote Neuroprotection by Inhibiting Neurovascular Dysfunction. Int J Alzheimer's Dis 2012:734956 (2012).

Pike et al. Neurodegeneration Induced by beta-Amyloid Peptides in vitro: The Role of Peptide Assembly State. J Neurosciences 13(4):1676-1687 (1993).

Porretta et al. Chemotherapeutic agents with an imidazole moiety. III. Synthesis and microbiologic activity of new 1,4-diaryllimidazole and 1,4-pyrrolimidazolephenylene derivatives. II Farmaco 46(7,8):913-924 (1991).

Pyorala et al. Diabetes and Atherosclerosis: An Epidemiologic View. Diabetes/Metabolism Reviews 3(2):463-524 (1987).

Ramasamy et al. Advanced glycation end products and RAGE: a common thread in aging, diabetes, neurodegeneration, and inflammation. Glycobiology 15:16R-18R (2005).

Rammes et al. Myeloid-related protein (MRP) 8 and MRP14, calcium-binding proteins of the S100 family, are secreted by activated monocytes via a novel, tubulin-dependent pathway. J. Biol. Chem. 272:9496-9502 (1997).

Ranginwala et al. Clinic Criteria for the Diagnosis of Alzheimer Disease: Still Good After I These Years. Am. J. Geriatr. Psychiatry 16(5):384-388 (2008).

Rauvala et al. Isolation and some characteristics of an adhesive factor of brain that enhances neurite outgrowth in central neurons. J. Biol. Chem. 262:16625-16635 (1987).

Reddy et al. N epsilon-(carboxymethyl)lysine is a dominant advanced glycation end product (AGE) antigen in tissue proteins. Biochem. 34:10872-10878 (1995).

Ritthaler et al. Expression of Receptors for Advanced Glycation End Products in Peripheral Occlusive Vascular Disease. Am J Pathol 146(3):688-694 (1995).

Robertson et al. Atherosclerosis in persons with Hypertension and Diabetes Mellitus. Laboratory investigation 18(5):538-551 (1968).

Rogaev et al. Familial Alzheimer's disease in kindreds with missense mutations in a gene on chromosome 1 related to the Alzheimer's disease type 3 gene. Nature 376:775-778 (1995).

Sabbagh et al. Abstract TTP488: From Futile to Fast Track. Presented at the 2015 Alzheimer's Association International Conference. Washington, DC, Jul. 2015.

Sabbagh et al. Abstract TTP488 Path to Registration: Leveraging Enrichment Strategies. Presented at the 2015 Alzheimer's Association International Conference. Washington. DC, Jul. 2015.

Sabbagh et al. PF-04494700, an Oral Inhibitor of Receptor for Advanced Glycation End Products (RAGE), in Alzheimer Disease. Alzheimer Dis Assoc Disord 25(3):206-12 (2011).

Sabbagh et al. Safety and efficacy results from the phase 3. multicenter, 18-month Steadfast tri of azeliragon in participants with mild Alzheimer's disease. Presented at 2018 CTAD. Oct. 26, 2018. Barcelona, Spain.

Sabbagh et al. TTP488 Path to Registration: Leveraging Enrichment Strategies. Presented at the 2015 Alzheimer's Association International Conference. Washington, DC, Jul. 2015.

Schafer et al. The S100 family of EF-hand calcium-binding proteins: functions and pathology. Trends Biochem Sci 21:134-140 (1996).

Schleicher et al. Increased accumulation of the glycoxidation product N(epsilon)-(carboxymethyl)lysine in human tissues in diabetes and aging. J. Clin. Invest. 99 (3):457-468 (1997).

Schmidt et al. Advanced Glycation Endproducts Interacting with Their Endothelial Receptor Induce Expression of Vascular Cell Adhesion Molecule-1 (VCAM-1) in Cultured Human Endothelial Cells and in Mice. J. Clin. Invest 96:1395-1403 (1995).

Schmidt et al. Receptor for advanced glycation end products (AGEs) has a central role in vessel wall interactions and gene activation in response to circulating AGE proteins. PNAS USA 91:8807-8811 (1994).

(56) References Cited

OTHER PUBLICATIONS

Schmidt et al. The V-Domain of Receptor for Advanced Glycation Endproducts (RAGE) Mediates Binding of Ages: A Novel Target for Therapy of Diabetic Complications. Supplement to Circulation 96(8):Abstract No. 194 (1997).
Schmidt et al. Isolation and Characterization of Two Binding Proteins for Advanced Glycosylation End Products from Bovine Lung Which are Present on the Endothelial Cell Surface. J Biol Chem 267(21):14987-14977 (1992).
Schmidt et al. The dark side of glucose. Nature Med. 1:1002-1004 (1995).
Selkoe. Normal and Abnormal Biology of the beta-Amyloid Precursor Protein. Annu Review of Neuroscience 17:489-517 (1994).
Selkoe. The Molecular Pathology of Alzheimer's Disease. Neuron 6:487-498 (1991).
Selkoe. Translating cell biology into therapeutic advances in Alzheimer's disease. Nature 399:A23-31 (1999).
Semprini et al. Evidence for differential S100 gene over-expression in psoriatic patients from genetically heterogeneous pedigrees. Hum. Genet. 111(4-5):310-3 (2002).
Sherrington et al. Cloning of a gene beating missense mutations in early-onset familial Alzheimer's disease. Nature 375:754-760 (1995).
Sims et al. HMGB1 and RAGE in inflammation and cancer. Annual Review of Immunology 28:367-368 (2010).
Snowdon. Healthy Aging and Dementia: Findings from the Nun Study. Annals of Intern Medicine 139(5):450-454 (2003).
Sousa et al. Interaction of the Receptor for Advanced Glycation End Products (RAGE) with Transthyretin Triggers Nuclear Transcription Factor kB (NF-kB) Activation. Laboratory Investigation 80(7):1101-1110 (2000).
Spite et al. Novel Lipid Mediators Promote Resolution of Acute Inflammation: Impact of Aspirin and Statins. Circulation Research 107:1170-1184 (2010).
Strittmatter et al. Apolipoprotein E: High-avidity binding to beta-amyloid and increased frequency of type 4 allele in late-onset familial Alzheimer disease. PNAS USA 90:1977-1981 (1993).
Taguchi et al. Blockade of RAGE-amphoterin signalling suppresses tumour growth and metastases. Nature 405:354-360 (2000).
Takuma et al. RAGE-mediated signing contributes to intraneuronal transport of amyloid-beta and neuron dysfunction. PNAS 106(47):20021-20026 (2009).
Tanaka et al. The receptor for advanced glycation end products is induced by the glycation products themselves and tumor necrosis factor-alpha through nuclear factor-kappa B, and by 17beta-estradiol through Sp-1 in human vascular endothelial cells. J. Biol. Chem. 275:25781-25790 (2000).
Teillet et al. Food restriction prevents advanced glycation end product accumulation and retards kidney aging in lean rats. J. Am. Soc. Nephrol 11:1488-1497 (2000).
Thompson. et al. Protein Conformation Misfolding and Amyloid Formation: Characteristics of a New Class of Disorders that Include Alzheimer's and Prion Diseases. Current Medicinal Chemistry 9:1751-1762 (2002).
Vellas et al. Long-term changes in ADAS-cog: What is clinically relevant for disease modifying trails in Alzheimer? J Nutr Health Aging 11(4):338-341 (2007).

Vlassara et al. Advanced Glycation End-products and Atherosclerosis. Ann. Med. 28:419-426 (1996).
VTv Therapeutics LLC. vTv Therapeutics Announces Topline Results from Part B of Phase 3 STEADFAST Study (Jun. 12, 2018) [Press Release].
VTv Therapeutics LLC. vTv Therapeutics Announces Topline Results from the First STEADFAST Phase 3 Study Evaluating Azeliragon in People with Mild Alzheimer's Disease (Apr. 9, 2018). [Press Release].
Waller et al. Status of the coronary arteries at necropsy in diabetes mellitus with onset after age 30 years. Analysis of 229 diabetic patients with and without clinical evidence of coronary heart disease and comparison to 183 control subjects. Am J Med 69:498-506 (1980).
Wang et al. The Profile of Soluble Amyloid beta Protein in Cultured Cell Media: Detection and Quantification of Amyloid beta Protein and Variants by immunoprecipitation—Mass Spectrometry. J Biol Chem 271(50):31894-31902 (1996).
Wautier et al. Advanced glycation end products (AGES) on the surface of diabetic erythrocytes bind to the vessel wall via a specific receptor inducing oxidant stress in the vasculature: A link between surface-associated AGEs and diabetic complications. PNAS USA 91:7742-7746 (1994).
Wautier et al. Receptor-mediated endothelial cell dysfunction in diabetic vasculopathy. Soluble receptor for advanced glycation end products blocks hyperpermeability in diabetic rats. J. Clin. Invest. 97:238-243 (1995.
Wisniewski et al. Apolipoprotein E: a pathologic chaperone protein in patients with cerebral and systemic amyloid. Neuroscience Letters 135:235-238 (1992).
Yan et al. Enhanced Cellular Oxidant Stress by the Interaction of Advanced Glycation End Products with Their Receptors/Binding Proteins. J Biol Chem 269(13):9889-9897 (1994).
Yan et al. RAGE and Alzheimer's Disease: A Progression Factor for Amyloid-beta-induced Cellular Perturbation? J Alzheimer's Dis 16:833-843 (2009).
Yan et al. Amyloid-beta peptide-receptor for advanced glycation endproduct interaction elicits neuronal expression of macrophage-colony stimulating factor: a proinflammatory pathway in Alzheimer disease. PNAS USA 94:5296-5301 (1997).
Yan et al. An intracellular protein that binds amyloid-beta peptide and mediates neurotoxicity in Alzheimer's disease. Nature 389:689-695 (1997).
Yan et al. RAGE and amyloid-beta peptide neurotoxicity in Alzheimer's disease. Nature 382:685-691 (1996).
Yan et al. Receptor-dependent cell stress and amyloid accumulation in systemic amyloidosis. Nat. Med. 6:643-651 (2000).
Yankner et al. Neurotrophic and Neurotoxic Effects of Amyloid beta Protein: Revers by Tachykinin Neuropeptides. Science 250(4978):279-282 (1990).
Yeh et al. Requirement for p38 and p44/p42 Mitogen-Activated Protein Kinases in RAGE-Mediated Nuclear Factor-kB Transcription Activation and Cytokine Secretion. Diabetes 50:1495-1504 (2001).
Zimmer et al. The S100 protein family: history, function, and expression. Brain Res. Bull. 37:417-429 (1995).

\* cited by examiner

CRYSTALLINE FORMS OF [3-(4-{2-BUTYL-1-[4-(4-CHLORO-PHENOXY)-PHENYL]-1H-IMIDAZOL-4-YL}-PHENOXY)-PROPYL]-DIETHYL-AMINE

FIELD OF THE INVENTION

The present invention relates to crystalline forms of [3-(4-{2-butyl-1-[4-(4-chloro-phenoxy)-phenyl]-1H-imidazol-4-yl}-phenoxy)-propyl]-diethylamine ("COMPOUND I"), and its use as a therapeutic agent.

BACKGROUND OF THE INVENTION

The Receptor for Advanced Glycation Endproducts (RAGE) is a member of the immunoglobulin super family of cell surface molecules. Activation of RAGE in different tissues and organs leads to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest.* 97:238-243 (1995)), nephropathy (Teillet et al., *J. Am. Soc. Nephrol.* 11: 1488-1497 (2000)), atherosclerosis (Vlassara et. al., *The Finnish Medical Society DUODECIM, Ann. Med.* 28:419-426 (1996)), and retinopathy (Hammes et al., *Diabetologia* 42:603-607 (1999)). RAGE has also been implicated in Alzheimer's disease (Yan et al., *Nature* 382: 685-691, (1996)), erectile dysfunction, and in tumor invasion and metastasis (Taguchi et al., *Nature* 405: 354-357, (2000)).

Binding of ligands such as advanced glycation endproducts (AGEs), 5100/calgranulin/EN-RAGE, β-amyloid, CML (NE-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras.

MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target, for down-regulation of the pathophysiological changes brought about by excessive concentrations of AGEs and other ligands for RAGE.

Polymorphs of a given substance have the same chemical composition, but may differ from each other with respect to one or more physical properties, such as solubility and dissociation, true density, melting point, crystal shape, compaction behavior, flow properties, and/or solid state stability. These differences affect practical parameters such as storage stability, compressibility and density (important in formulation and product manufacturing), and dissolution rates (an important factor in determining bio-availability). Although U.S. Pat. No. 7,884,219 discloses Form I and Form II of COMPOUND I, there is a need for additional drug forms that are useful for inhibiting RAGE activity in vitro and in vivo, and have properties suitable for large-scale manufacturing and formulation. Provided herein are new polymorphs of COMPOUND I, as well as methods of producing the polymorphs COMPOUND I.

SUMMARY OF THE INVENTION

The preparation of [3-(4-{2-butyl-1-[4-(4-chloro-phenoxy)-phenyl]-1H-imidazol-4-yl}-phenoxy)-propyl]-diethyl-amine ("COMPOUND I") and the use thereof, such as an antagonist of the receptor for advanced glycation endproducts (RAGE) and in the treatment of various medical conditions, are described in US Patent Publication No. 2004-0082542 and in US Patent Publication No. 2005-0026811. Such diseases or disease states may include, but are not limited to, acute and chronic inflammation, amyloidosis, Alzheimer's disease, cancer, tumor invasion and metastasis, kidney failure, or inflammation associated with autoimmunity, inflammatory bowel disease, rheumatoid arthritis, psoriasis, multiple sclerosis, hypoxia, stroke, heart attack, hemorrhagic shock, sepsis, organ transplantation, the development of diabetic late complications such as increased vascular permeability, diabetic nephropathy, diabetic retinopathy, a diabetic foot ulcer, a cardiovascular complication, diabetic neuropathy, impaired wound healing, erectile dysfunction, and osteoporosis. COMPOUND I and a method for its preparation are exemplified in US Patent Publication No. 2004-0082542 in Example 406.

In one aspect, the present invention provides polymorphic forms of COMPOUND I. In one embodiment, the present invention provides a first polymorph, Form III, of COMPOUND I. In another embodiment, the present invention provides a second polymorph, Form IV, of COMPOUND I. In another aspect, the present invention provides methods for producing Form III and Form IV polymorphs of COMPOUND I.

In another aspect, the present invention provides a pharmaceutical composition comprising one or more of Form I, Form II, Form III, and Form IV of COMPOUND I.

In another aspect, the present invention provides a method of producing a pharmaceutical composition comprising one or more of Form I, Form II, Form III, and Form IV of COMPOUND I.

In another aspect, the present invention provides a method of treating one or more RAGE mediated diseases comprising administering one or more of Form I, Form III, and Form IV of COMPOUND I to a subject in need thereof. Embodiments of the method of treatment of the present invention may comprise administering a pharmaceutical composition comprising a therapeutically effective amount of one or more polymorphs of COMPOUND I These and other embodiments of the present invention are described in greater detail in the detailed description of the invention which follows.

DETAILED DESCRIPTION

Figure 1:
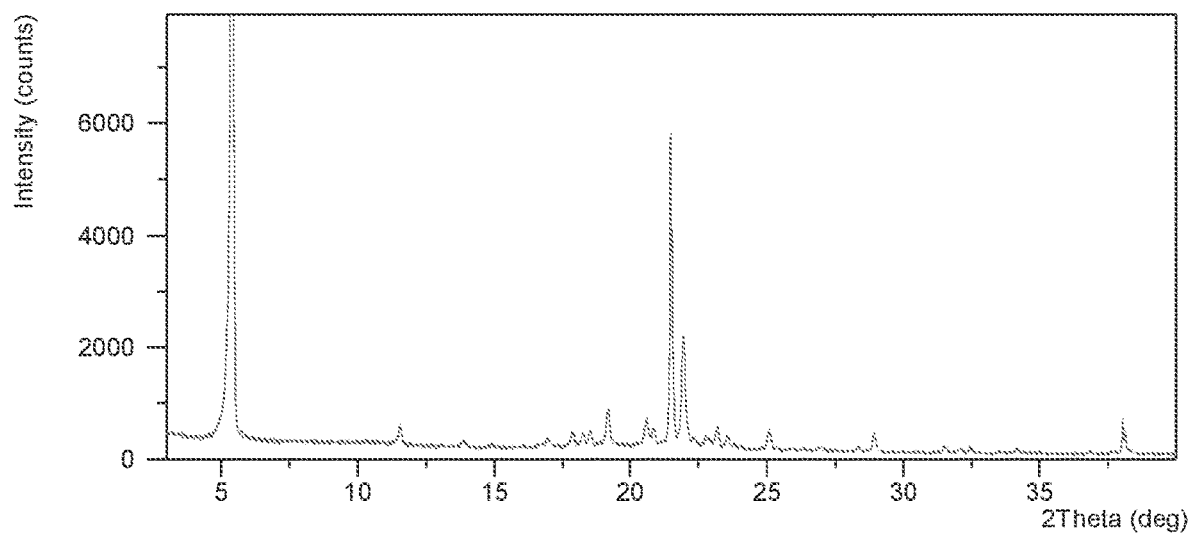
FIG. 1 is a Powder X-ray Powder Diffraction Pattern of Form III.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

By percent by weight it is meant that a particular weight of one ingredient in a composition is divided by the total weight of all of the ingredients in that composition. Percent by weight may be used interchangeably and means approximately the same as weight/weight percent or % (weight/weight) or percent by mass or mass percent. When a liquid solute is used, it is often more practical to use volume/volume percent or % (vol/vol) or percent by volume, which are all considered to be synonymous. Ppm (parts per million), ppb (parts per billion), pph (parts per hundred) are often used to indicate a percentage based on quantity and not on mass (i.e., the quantity of a given type of atom or a given type of molecule in a composition with more atoms or molecules (be it gas, liquid or solid) is divided by the total quantity of atoms or molecules in the total composition). Other terms that are used are molarity, which is the number of moles of solute per liters of solution, and molality, which is the number of moles of solution per kilograms of solution. Another concentration unit is the mole fraction, which is the moles of a given component divided by the total moles of all solution components. Mole percent is related to the mole fraction and is the mole fraction multiplied by 100.

It is further noted that, as used in this specification, the singular forms "a," "an," and "the" include plural referents unless expressly and unequivocally limited to one referent.

The term "RAGE mediated disease" is used herein to refer to one or more conditions, diseases or disease states including, but not limited to, acute or chronic inflammation including skin inflammation such as psoriasis, rheumatoid arthritis, atopic dermatitis and lung inflammation including, asthma and chronic obstructive pulmonary disease, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease including inflammation associated with autoimmunity or organ, tissue, or cell transplant, impaired wound healing, periodontal disease, neuropathy, neuronal degeneration, vascular permeability, nephropathy, atherosclerosis, retinopathy, Alzheimer's disease, erectile dysfunction, tumor invasion and/or metastasis, osteoporosis, and the development of diabetic late complications such as increased vascular permeability, nephropathy, retinopathy, and neuropathy. The pharmaceutical compositions comprising a polymorphic form of COMPOUND I also may be used to antagonize RAGE in a subject.

The term "therapeutically effective amount" is used herein to denote the amount of the polymorph of COMPOUND I that will elicit the therapeutic response of a subject that is being sought. In an embodiment, the therapeutic response may be antagonizing RAGE.

Embodiments of the invention are directed to polymorphs of COMPOUND I, wherein the particular polymorph (e.g., Form III, Form IV) has at least a particular percentage of purity. In some embodiments of the invention, the polymorph of COMPOUND I (e.g., Form III, Form IV) is at least 80% pure. In some embodiments of the invention, the polymorph of COMPOUND I (e.g., Form III, Form IV) is at least 85% pure. In some embodiments of the invention, the polymorph of COMPOUND I (e.g., Form III, Form IV) is at least 90% pure. In some embodiments of the invention, the polymorph of COMPOUND I (e.g., Form III, Form IV) is at least 95% pure. In some embodiments of the invention, the polymorph of COMPOUND I (e.g., Form III, Form IV) is substantially free of other polymorphic forms. As used herein, a first polymorphic form that is "substantially pure" of other polymorphic forms includes the complete absence of the second form or an amount of the second form that is not readily detectable by ordinary analytical methods. Such ordinary analytical methods include DSC, solid state $^{13}$C NMR, Raman, X-ray powder diffraction, mid-IR (such as FT-IR) and near-IR. In an embodiment, an amount of a polymorphic form that is not readily detectable by one or more ordinary analytical methods is less than 5 percent by weight. In another embodiment, the amount of a polymorphic form that is not readily detectable by one or more ordinary analytical methods is less than 3 percent by weight. In another embodiment, the amount of a polymorphic form that is not readily detectable by one or more ordinary analytical methods is less than 2 percent by weight. In another embodiment, the amount of a polymorphic form that is not readily detectable by one or more ordinary analytical methods is less than 1 percent by weight. In another embodiment, the amount of a polymorphic form that is not readily detectable by one or more ordinary analytical methods is less than 0.5 percent by weight.

In another embodiment, the dosage or blood level of COMPOUND I and administration may be sufficient for inhibition of the biological function of RAGE at a sufficient level for sufficient time to reverse amyloidosis.

A therapeutically effective amount may be achieved in a subject by administering a dosage level of less 100 mg of compound per day. In another embodiment, the dosage level of administration is greater than 1 mg of compound per day. In another embodiment, the dosage level of administration is 5, 10 or 20 mg of compound per day.

The term "treatment" as used herein, refers to the full spectrum of treatments for a given condition or disorder from which a subject is suffering, including alleviation or amelioration of one or more of the symptoms resulting from that disorder, to the delaying of the onset or progression of the disorder.

In one aspect, the present invention provides polymorphs, or mixtures thereof, of COMPOUND I.

One embodiment of the present invention is a solid state form of [3-(4-{2-butyl-1-[4-(4-chlorophenoxy)phenyl]-1H-imidazol-4-yl}phenoxy)-propyl]-diethylamine, wherein the solid state form is selected from the group consisting of:

a) a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 5.4°, 21.5°, and 22.0°±0.2°; and b) a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 19.7°, 22.0°, and 30.2°±0.2°.

Figure 2:
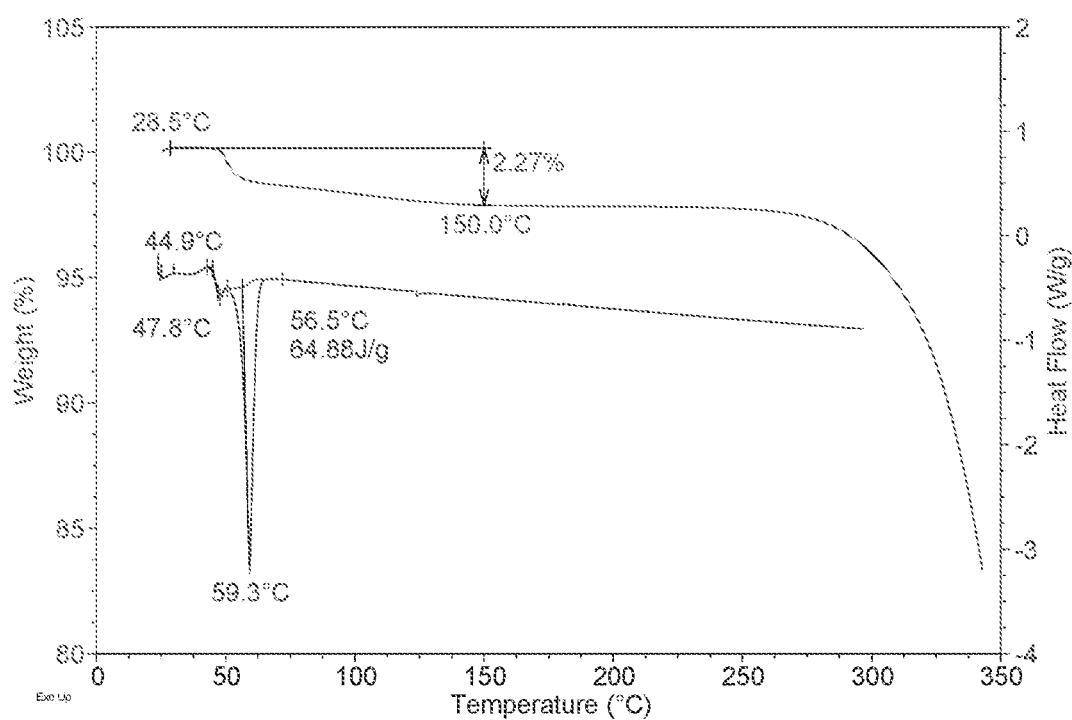
FIG. 2 is a Differential Scanning calorimetry ("DSC") profile and a Thermogravimetric Analysis ("TGA") of Form III.

In one embodiment, the solid state form is characterized by an XRPD pattern having peaks at 2θ angles of 5.4°, 21.5°, and 22.0°±0.2°. In one embodiment, the solid state form is characterized by an XRPD pattern as shown in FIG. 1. In one embodiment, the solid state form is characterized by an endothermic peak at about 59° C., as determined by DSC. In one embodiment, the solid state form is characterized by a DSC profile as shown in FIG. 2. In one embodiment, the solid state form is characterized by an about 2.3 wt % loss between room temperature and about 150° C., as determined by TGA. In one embodiment, the solid state form is characterized by TGA profile as shown in FIG. 2. In one embodiment, the solid state form is characterized by at least two of the following features (i)-(iii):

i) an XRPD pattern having peaks at 2θ angles of 5.4°, 21.5°, and 22.0°±0.2°;

ii) a DSC profile as shown in FIG. 2; or iii) a TGA profile as shown in FIG. 2.

In one embodiment, the solid state form is Form III of [3-(4-{2-butyl-1-[4-(4-chlorophenoxy)phenyl]-1H-imidazol-4-yl}phenoxy)-propyl]-diethylamine.

Figure 3:
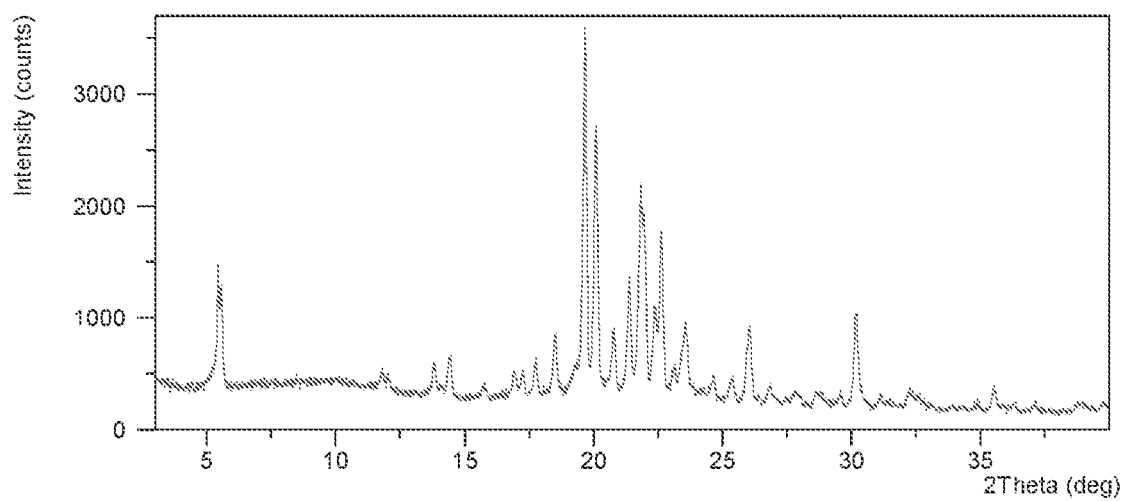
FIG. 3 is a Powder X-ray Powder Diffraction Pattern of Form IV.
Figure 4:
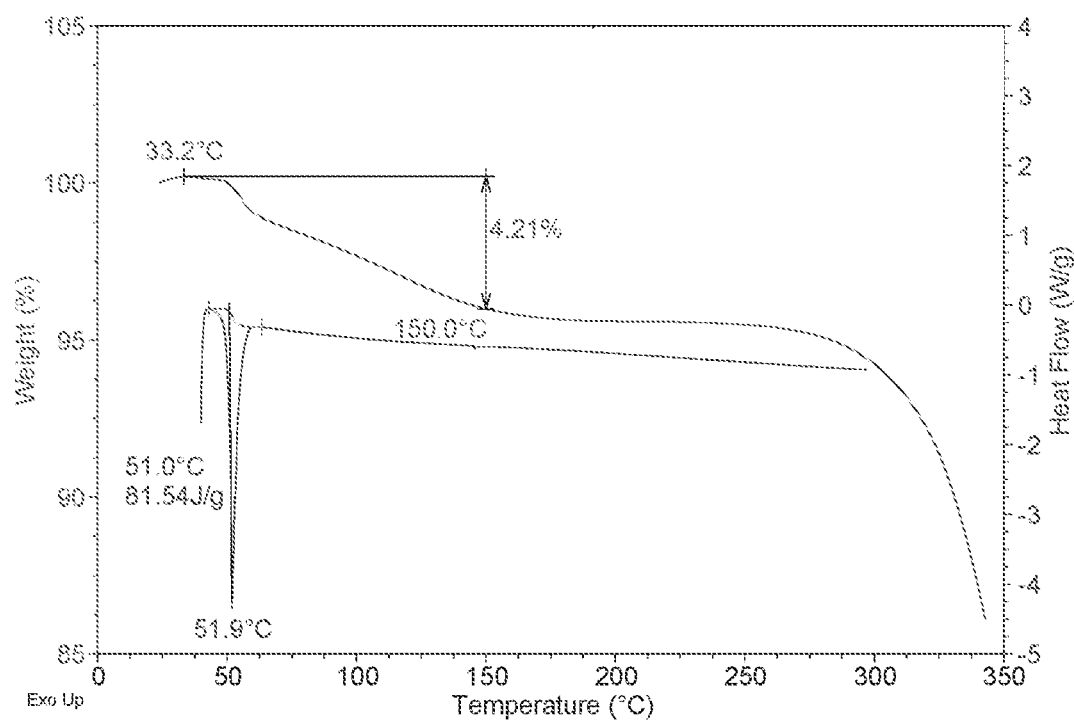
FIG. 4 is a Differential Scanning calorimetry ("DSC") profile and a Thermogravimetric Analysis ("TGA") of Form IV.

In another embodiment, the solid state form is characterized by an XRPD pattern having peaks at 2θ angles of 19.7°, 22.0°, and 30.2°±0.2°. In another embodiment, the solid state form is characterized by an XRPD pattern having peaks at 2θ angles of 5.4, 19.7°, 21.8, 22.0°, and 30.2°±0.2°. In another embodiment, the solid state form is characterized by an XRPD pattern as shown in FIG. 3. In another embodiment, the solid state form is characterized by an endothermic peak at about 51.9° C., as determined by DSC. In another embodiment, the solid state form is characterized by a DSC profile as shown in FIG. 4. In another embodiment, the solid state form is characterized by an about 4.2 wt % loss between room temperature and about 150° C., as determined by TGA. In another embodiment, the solid state form is characterized by a TGA profile as shown in FIG. 4. In another embodiment, the solid state form is characterized by at least two of the following features (i)-(iii):

(i) an XRPD pattern having peaks at 2θ angles of 19.7°, 22.0°, and 30.2°±0.2°;

(ii) a DSC profile as shown in FIG. 4; or (iii) a TGA profile as shown in FIG. 4.

In another embodiment, the solid state form is Form IV.

For all embodiments disclosed herein, a peak positional reproducibility is associated with the values of degree-2θ (XRPD), ppm ($^{13}$C solid state NMR), and $cm^{-1}$ (IR and Raman). Accordingly, it will be understood that all peaks disclosed herein have the value disclosed ± the peak positional reproducibility associated with each analytical technique. The XRPD peak positional reproducibility is ±0.2 expressed in degree-2θ. The $^{13}$C NMR peak positional reproducibility is ±0.2 ppm. The IR peak positional reproducibility is ±2 $cm^{-1}$. The Raman peak positional reproducibility is ±2 $cm^{-1}$.

Forms of Compound I

Form I

Crystalline Form I is characterized by the following X-ray powder diffraction pattern expressed in terms of the degree 2θ and relative intensities with a relative intensity of ≥3.4% measured on a Bruker D5000 diffractometer with CuKα radiation:

X-Ray Powder Diffraction Peaks for Crystalline Form I

| Angle (Degree 2θ) | Relative Intensity* % |
|---|---|
| 4.6 | 5.7 |
| 5.5 | 3.9 |
| 6.8 | 67.0 |
| 9.1 | 12.3 |
| 10.2 | 35.4 |
| 11.2 | 4.5 |
| 11.6 | 8.3 |
| 13.1 | 3.4 |
| 13.7 | 21.9 |
| 14.6 | 5.3 |
| 15.0 | 6.3 |
| 15.4 | 5.9 |
| 15.9 | 10.8 |
| 16.5 | 16.5 |
| 17.4 | 70.6 |
| 18.4 | 11.5 |
| 19.0 | 13.9 |
| 20.7 | 100.0 |
| 21.3 | 77.3 |
| 21.7 | 37.4 |
| 22.4 | 22.0 |
| 22.8 | 11.2 |
| 23.1 | 8.2 |
| 23.4 | 8.2 |
| 23.7 | 7.8 |
| 24.2 | 8.0 |
| 24.7 | 32.8 |
| 24.9 | 37.5 |
| 25.3 | 30.1 |
| 26.3 | 28.9 |
| 26.8 | 9.5 |
| 27.2 | 10.6 |
| 28.0 | 9.5 |
| 29.8 | 7.9 |
| 30.9 | 6.8 |
| 32.1 | 11.0 |
| 33.0 | 6.0 |
| 34.1 | 8.4 |
| 34.8 | 5.9 |
| 37.3 | 9.5 |
| 38.0 | 4.9 |
| 38.7 | 5.8 |

Representative values of degree 2θ for Form I are 13.1, 16.5, 22.4 and 26.8. Particularly representative values of degree 2θ for Form I are 16.5 and 26.8.

Crystalline Form I is characterized by the following $^{13}$C Solid State NMR shifts.

| $^{13}$C Chemical Shifts$^a$ [ppm] | Intensity$^b$ |
|---|---|
| 158.7 | 8.6 |
| 157.9 | 10.6 |
| 153.0 | 8.2 |
| 149.7 | 9.4 |
| 141.0 | 8.5 |
| 132.4 | 10.1 |
| 131.4 | 8.9 |
| 127.6 | 12.0 |
| 125.9 | 4.5 |
| 125.0 | 5.0 |
| 117.4 | 3.3 |
| 114.2 | 6.3 |
| 110.8 | 2.0 |
| 65.6 | 8.0 |
| 52.0 | 8.5 |
| 46.6 | 4.6 |
| 33.8 | 8.3 |
| 27.6 | 11.4 |
| 27.2 shoulder | — |
| 24.1 | 10.4 |

-continued

| $^{13}$C Chemical Shifts$^a$ [ppm] | Intensity$^b$ |
|---|---|
| 16 | 11.9 |
| 13.9 | 10.2 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Representative $^{13}$C NMR chemical shifts for Form I are as follows:

| Form I $^{13}$C Chemical Shifts [ppm] |
|---|
| 157.9 |
| 153.0 |
| 149.7 |
| 141.0 |
| 131.4 |
| 33.8 |
| 27.6 |
| 13.9 |

Form I is characterized by the following FT-IR peaks:

FT-IR Peak List of Form I

| Wavelength (cm$^{-1}$) |
|---|
| 652 |
| 675 |
| 697 |
| 715 |
| 749 |
| 777 |
| 829 |
| 853 |
| 870 |
| 898 |
| 919 |
| 945 |
| 958 |
| 1016 |
| 1067 |
| 1086 |
| 1105 |
| 1162 |
| 1200 |
| 1223 |
| 1236 |
| 1279 |
| 1294 |
| 1318 |
| 1353 |
| 1379 |
| 1408 |
| 1429 |
| 1444 |
| 1465 |
| 1486 |
| 1503 |
| 1563 |
| 1576 |
| 1588 |
| 1617 |
| 1882 |
| 1899 |
| 1981 |
| 2051 |
| 2163 |
| 2276 |
| 2324 |
| 2391 |
| 2672 |

-continued

| Wavelength (cm$^{-1}$) |
|---|
| 2731 |
| 2803 |
| 2813 |
| 2869 |
| 2900 |
| 2927 |
| 2961 |
| 3033 |
| 3061 |
| 3093 |
| 3133 |

Representative FT-IR peaks for Form I are as follows:

| Form I Length (cm$^{-1}$) |
|---|
| 697 |
| 870 |
| 1016 |
| 1223 |

Form I is characterized by the following Raman peaks:

Representative Raman Peaks of Form I

| Form I Wavenumber (cm$^{-1}$) |
|---|
| 139 |
| 192 |
| 198 |
| 208 |
| 217 |
| 266 |
| 293 |
| 335 |
| 371 |
| 389 |
| 422 |
| 448 |
| 475 |
| 511 |
| 525 |
| 571 |
| 620 |
| 633 |
| 653 |
| 677 |
| 698 |
| 724 |
| 753 |
| 787 |
| 798 |
| 821 |
| 834 |
| 855 |
| 871 |
| 880 |
| 898 |
| 947 |
| 1004 |
| 1010 |
| 1024 |
| 1055 |
| 1075 |
| 1088 |
| 1106 |
| 1170 |
| 1197 |
| 1250 |
| 1274 |
| 1293 |

-continued

| Form I Wavenumber (cm$^{-1}$) |
| --- |
| 1318 |
| 1354 |
| 1362 |
| 1410 |
| 1430 |
| 1444 |
| 1497 |
| 1510 |
| 1563 |
| 1586 |
| 1618 |
| 2571 |
| 2871 |
| 2902 |
| 2932 |
| 2962 |
| 3063 |

Particularly representative Raman peaks for Form I are as follows:

| Form I Wavenumber (cm$^{-1}$) |
| --- |
| 266 |
| 293 |
| 335 |
| 653 |
| 787 |
| 1497 |

Thermogravimetric analysis of Form I showed negligible weight loss of approximately 0.1% wt/wt or less from 25 to 250° C.

Form II

Crystalline Form II is characterized by the following X-ray powder diffraction pattern expressed in terms of the degree 2θ and relative intensities with a relative intensity of 6.0% measured on a Bruker D5000 diffractometer with CuKα radiation:

X-Ray Powder Diffraction Peaks for Crystalline Form II

| Angle (Degree 2-θ) | Relative Intensity* % |
| --- | --- |
| 4.5 | 17.8 |
| 6.7 | 63.3 |
| 9.1 | 14.1 |
| 10.0 | 10.8 |
| 10.3 | 12.4 |
| 11.0 | 6.0 |
| 11.6 | 15.1 |
| 12.5 | 7.0 |
| 13.6 | 14.0 |
| 14.5 | 11.2 |
| 15.1 | 29.9 |
| 15.7 | 15.0 |
| 17.5 | 40.4 |
| 18.3 | 41.8 |
| 18.8 | 87.1 |
| 19.7 | 9.8 |
| 20.1 | 34.5 |
| 20.6 | 84.4 |
| 21.0 | 15.6 |
| 21.6 | 100.0 |
| 22.1 | 36.3 |
| 22.7 | 20.8 |
| 23.1 | 52.0 |
| 23.6 | 77.1 |
| 24.3 | 17.7 |
| 24.8 | 12.4 |
| 25.5 | 14.4 |
| 25.8 | 17.0 |
| 26.2 | 59.1 |
| 27.3 | 17.5 |
| 28.2 | 12.8 |
| 28.7 | 6.8 |
| 29.5 | 26.9 |
| 30.0 | 7.4 |
| 30.4 | 6.9 |
| 31.2 | 6.8 |
| 31.6 | 7.3 |
| 32.1 | 16.7 |
| 32.5 | 9.8 |
| 32.9 | 8.5 |
| 33.2 | 12.5 |
| 33.7 | 9.0 |
| 34.3 | 8.4 |
| 35.2 | 7.3 |
| 35.7 | 7.6 |
| 37.4 | 7.8 |
| 38.3 | 10.4 |
| 39.6 | 9.6 |

*The relative intensities may change depending on the crystal size and morphology.

Representative values of degree 2θ for Form II are 18.8 and 20.1±0.2.

Form II is characterized by the following $^{13}$C Solid State NMR chemical shifts:

| $^{13}$C Chemical Shifts$^a$ [ppm] | Intensity$^b$ |
| --- | --- |
| 158.6 | 5.0 |
| 153.6 | 12.0 |
| 149.0 | 6.1 |
| 140.1 | 5.7 |
| 133.0 | 6.1 |
| 132.3 | 3.6 |
| 128.9 | 5.4 |
| 127.6 | 5.4 |
| 126.8 | 6.5 |
| 125.6 | 8.0 |
| 123.2 | 4.1 |
| 121.6 | 5.3 |
| 119.9 | 5.1 |
| 114.4 | 8.4 |
| 110.5 | 3.9 |
| 67.4 | 3.5 |
| 51.8 | 1.7 |
| 29.6 | 5.4 |
| 28.6 | 6.7 |
| 23.8 | 4.1 |
| 15.5 | 6.1 |
| 9.4 | 1.7 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Representative chemical shifts for Form II are as follows:

| Form II $^{13}$C Chemical Shifts [ppm] |
| --- |
| 153.6 |
| 149.0 |
| 140.1 |
| 123.2 |
| 121.6 |
| 119.9 |
| 28.6 |

Form II is characterized by the following FT-IR peaks:

FT-IR Peak Lists of Form II

| Wavelength (cm$^{-1}$) |
|---|
| 660 |
| 675 |
| 690 |
| 707 |
| 717 |
| 735 |
| 750 |
| 762 |
| 783 |
| 816 |
| 824 |
| 836 |
| 848 |
| 877 |
| 899 |
| 916 |
| 928 |
| 945 |
| 969 |
| 1004 |
| 1024 |
| 1046 |
| 1062 |
| 1075 |
| 1088 |
| 1105 |
| 1115 |
| 1135 |
| 1159 |
| 1178 |
| 1202 |
| 1239 |
| 1274 |
| 1290 |
| 1316 |
| 1325 |
| 1368 |
| 1395 |
| 1412 |
| 1425 |
| 1455 |
| 1462 |
| 1482 |
| 1502 |
| 1563 |
| 1576 |
| 1587 |
| 1617 |
| 1773 |
| 1898 |
| 1981 |
| 2022 |
| 2038 |
| 2052 |
| 2070 |
| 2164 |
| 2191 |
| 2259 |
| 2288 |
| 2324 |
| 2677 |
| 2725 |
| 2774 |
| 2783 |
| 2823 |
| 2865 |
| 2881 |
| 2898 |
| 2926 |
| 2950 |
| 2958 |
| 3030 |
| 3047 |
| 3061 |
| 3078 |
| 3090 |
| 3140 |

Representative FT-IR peaks for Form II are as follows:

| Form II Wavelength (cm$^{-1}$) |
|---|
| 660 |
| 707 |
| 735 |
| 816 |
| 969 |
| 1024 |
| 1046 |
| 1135 |
| 1178 |

Form II is characterized by the following Raman peaks:

Representative Raman Peaks of Form II

| Form II Wavenumber (cm$^{-1}$) |
|---|
| 137 |
| 156 |
| 193 |
| 257 |
| 277 |
| 300 |
| 326 |
| 374 |
| 395 |
| 419 |
| 435 |
| 443 |
| 465 |
| 474 |
| 483 |
| 506 |
| 520 |
| 536 |
| 567 |
| 590 |
| 621 |
| 634 |
| 646 |
| 660 |
| 676 |
| 693 |
| 708 |
| 722 |
| 750 |
| 772 |
| 795 |
| 825 |
| 837 |
| 852 |
| 878 |
| 900 |
| 915 |
| 947 |
| 1005 |
| 1027 |
| 1061 |
| 1089 |
| 1106 |
| 1134 |
| 1160 |
| 1180 |

| Form II Wavenumber (cm$^{-1}$) |
| --- |
| 1196 |
| 1223 |
| 1243 |
| 1277 |
| 1298 |
| 1324 |
| 1348 |
| 1370 |
| 1412 |
| 1441 |
| 1454 |
| 1467 |
| 1507 |
| 1563 |
| 1575 |
| 1589 |
| 1617 |
| 2728 |
| 2783 |
| 2825 |
| 2868 |
| 2879 |
| 2917 |
| 2931 |
| 2957 |
| 3014 |
| 3031 |
| 3066 |
| 3137 |
| 3174 |
| 3226 |

Particularly representative Raman peaks for Form II are as follows:

| Form II Wavenumber (cm$^{-1}$) |
| --- |
| 257 |
| 300 |
| 326 |
| 590 |
| 646 |
| 1180 |
| 1348 |
| 1370 |

Thermogravimetric analysis showed negligible weight loss of approximately 0.1% wt/wt or less for Form II from 25 to 250° C.

Form III

Crystalline Form III is characterized by the following X-ray powder diffraction pattern expressed in terms of the degree 2θ:

X-Ray Powder Diffraction Peaks for Crystalline Form III

| Angle (Degree 2-θ) | Relative Intensity* % |
| --- | --- |
| 5.4 | 100.0 |
| 11.5 | 1.12 |
| 13.9 | 0.26 |
| 14.9 | 0.18 |
| 17.0 | 0.62 |
| 17.9 | 1.00 |
| 18.3 | 0.98 |
| 18.5 | 1.05 |
| 19.2 | 2.34 |
| 20.6 | 1.97 |
| 20.8 | 1.28 |
| 21.5 | 20.69 |
| 21.6 | 12.94 |
| 22.0 | 7.25 |
| 23.4 | 0.77 |
| 22.8 | 0.67 |
| 23.2 | 1.47 |
| 23.5 | 0.95 |
| 25.1 | 1.30 |
| 26.9 | 0.24 |
| 28.3 | 0.25 |
| 28.9 | 1.12 |
| 31.5 | 0.45 |
| 32.0 | 0.24 |
| 32.5 | 0.41 |
| 34.2 | 0.31 |
| 36.8 | 0.14 |
| 38.0 | 2.11 |
| 38.1 | 1.14 |

*The relative intensities may change depending on the crystal size and morphology.

Representative values of degree 2θ for Form III are 5.4, 21.5, and 22.0±0.2.

Thermogravimetric analysis (TGA) and Differential Scanning calorimetry (DSC) data displayed in FIG. 2 indicated a weight loss of 2.3 up to 150° C. and one sharp melting peak at 59.3° C. (peak temperature).

Form IV

Crystalline Form IV is characterized by the following X-ray powder diffraction pattern expressed in terms of the degree 2θ:

X-Ray Powder Diffraction Peaks for Crystalline Form IV

| Angle (Degree 2-θ) | Relative Intensity* % |
| --- | --- |
| 5.4 | 30.74 |
| 5.6 | 25.70 |
| 10.0 | 1.66 |
| 11.8 | 5.45 |
| 13.8 | 8.16 |
| 14.5 | 10.26 |
| 15.8 | 3.56 |
| 16.9 | 7.21 |
| 17.3 | 7.59 |
| 17.8 | 10.42 |
| 18.5 | 16.85 |
| 19.7 | 100.00 |
| 20.1 | 74.55 |
| 20.8 | 18.82 |
| 21.4 | 33.93 |
| 21.8 | 57.45 |
| 22.0 | 40.75 |
| 22.4 | 25.84 |
| 22.6 | 47.39 |
| 23.1 | 9.74 |
| 23.6 | 20.86 |
| 24.7 | 7.19 |
| 25.4 | 7.37 |
| 26.1 | 21.01 |
| 26.9 | 5.48 |
| 27.8 | 3.76 |
| 28.6 | 3.36 |
| 29.6 | 3.17 |
| 30.1 | 25.18 |
| 30.2 | 25.58 |
| 31.2 | 3.57 |
| 32.2 | 4.65 |
| 34.9 | 1.84 |
| 35.5 | 6.50 |

-continued

| Angle (Degree 2-θ) | Relative Intensity* % |
|---|---|
| 36.3 | 2.11 |
| 37.1 | 1.96 |
| 39.0 | 2.14 |

*The relative intensities may change depending on the crystal size and morphology.

Representative values of degree 2θ for Form IV are 19.7, 22.0, and 30.2±0.2.

TGA and DSC data displayed in FIG. 4 indicated a weight loss of 4.2% up to 150° C. and one sharp possible desolvation/melting peak at 51.9° C. (peak temperature).

Methods of Making

COMPOUND I and a method for its preparation are exemplified in US Patent Publication No. 2004-0082542 in Example 406, herein incorporated by reference. Additional methods to prepare COMPOUND I are described in U.S. Pat. No. 7,884,219, herein incorporated by reference. In another aspect, the present invention provides a method for producing a polymorph of COMPOUND I.

In one embodiment, the method involves producing solid state form Form III of [3-(4-{2-butyl-1-[4-(4-chlorophenoxy)phenyl]-1H-imidazol-4-yl}phenoxy)-propyl]-diethylamine, wherein the method comprises:

a) dissolving a suitable amount of [3-(4-{2-butyl-1-[4-(4-chlorophenoxy)phenyl]-1H-imidazol-4-yl}phenoxy)-propyl]-diethylamine in a suitable amount of a suitable solvent at room temperature to make a solution;

b) allowing the solution from step a) to evaporate at room temperature; and c) collecting the solid produced from step b).

In one embodiment, the suitable solvent in step a) is 2-methyltetrahydrofuran or tetrahydrofuran.

In another embodiment, the present invention provides a method for producing solid state form Form III of [3-(4-{2-butyl-1-[4-(4-chlorophenoxy)phenyl]-1H-imidazol-4-yl}phenoxy)-propyl]-diethylamine, wherein the method comprises:

a) dissolving a suitable amount of [3-(4-{2-butyl-1-[4-(4-chlorophenoxy)phenyl]-1H-imidazol-4-yl}phenoxy)-propyl]-diethylamine in a suitable amount of a suitable solvent at room temperature to make a solution;

b) stirring the solution from step a);

c) adding a suitable amount of a suitable anti-solvent; and d) collecting the solid product produced from step c).

In one embodiment, the suitable solvent in step a) is selected from the group consisting of ethanol, n-propyl alcohol, isopropyl alcohol, 2-methyltetrahydrofuran, isopropyl acetate, and methyl ethyl ketone. In one embodiment, the suitable anti-solvent in step c) is selected from the group consisting of water, hexane, and n-heptane.

In yet another embodiment, the method involves producing of solid state form Form III of [3-(4-{2-butyl-1-[4-(4-chlorophenoxy)phenyl]-1H-imidazol-4-yl}phenoxy)-propyl]-diethylamine, wherein the method comprises:

a) slurrying a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at a suitable temperature; and b) collecting the solid produced from step a).

In one embodiment, the suitable solvent system in step a) is selected from the group consisting of isopropyl alcohol, ethanol, ethyl acetate, cyclopentyl methyl ether, acetone, ethanol/water, n-propyl alcohol/heptane, ethanol/hexane, methyl ethyl ketone/hexane, 4-methyl-2-pentanone/hexane, isopropyl alcohol/hexane, ethyl acetate/hexane, toluene/hexane, 2-methyltetrahydrofuran/hexane, dioxane/hexane, cyclohexane, anisole, anisole/hexane, and methyl tert-butyl ether/hexane. In one embodiment, the suitable temperature is room temperature or 35° C.

In still yet another embodiment, the method involves producing solid state form Form III of [3-(4-{2-butyl-1-[4-(4-chlorophenoxy)phenyl]-1H-imidazol-4-yl}phenoxy)-propyl]-diethylamine, wherein the method comprises:

a) dissolving a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at room temperature to make a solution;

b) adding a suitable amount of a polymer mixture to the solution from step a) to make a suspension;

c) allowing the suspension of step b) to evaporate at room temperature; and d) collecting the solid produced from step c).

In one embodiment, the suitable solvent system in step a) is selected from the group consisting of isopropyl alcohol, cyclohexane, ethyl acetate/hexane, acetone/hexane, isopropyl acetate/hexane, methyl ethyl ketone/hexane, and n-propyl alcohol/water. In one embodiment, the polymer mixture in step b) is selected from the group consisting of polyvinylpyrrolidone/polyvinyl alcohol/polyvinyl chloride/hypromellose/methyl cellulose or poly(methyl methacrylate)/sodium alginate/hydroxyethyl cellulose.

In another embodiment, the method involves producing solid state form Form III of [3-(4-{2-butyl-1-[4-(4-chlorophenoxy)phenyl]-1H-imidazol-4-yl}phenoxy)-propyl]-diethylamine, wherein the method comprises:

a) dissolving a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at room temperature to make a solution in a vessel;

b) adding a suitable amount of a volatile solvent to the vessel of step a);

c) sealing the vessel after step b);

d) maintaining the vessel at room temperature for a sufficient amount of time for the volatile solvent to interact with the solution; and e) collecting the solid produced from step c).

In one embodiment, the suitable solvent system in step a) is methyl ethyl ketone and the suitable volatile solvent is hexane.

In yet another embodiment, the method involves producing solid state form Form III of [3-(4-{2-butyl-1-[4-(4-chlorophenoxy)phenyl]-1H-imidazol-4-yl}phenoxy)-propyl]-diethylamine, wherein the method comprises:

a) suspending a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at room temperature to make a suspension;

b) heating the suspension from step a) to a suitable temperature and equilibrating for a suitable amount of time;

c) optionally filtering the suspension from step b);

d) slowly cooling to a suitable temperature over a suitable amount of time; and e) collecting the solid produced from step d).

In one embodiment, the suitable solvent system in step a) is selected from the group consisting of isopropyl alcohol, acetonitrile, cyclohexane, n-butanol, ethanol/n-heptane, methyl ethyl ketone/n-heptane, isopropyl alcohol/n-heptane, methyl tert-butyl ether/n-heptane, trichloromethane/hexane, isopropyl alcohol/hexane, methyl tert-butyl ether/hexane, ethyl acetate/hexane, toluene/hexane, and cyclopentyl methyl ether/hexane. In one embodiment the suitable temperature is about 40° C. and the suitable amount of time is about 1 hour in step b). In one embodiment, the suitable temperature is about 5° C. and the suitable time is about 5.5 hours in step d). In one embodiment, if no solid is obtained after cooling to about 5° C., a further cooling to −20° C. step is performed. In one embodiment, if no solid is obtained after cooling to about 5° C., an evaporation at room temperature step is performed.

In still yet another embodiment, the method involves producing solid state form Form III of [3-(4-{2-butyl-1-[4-(4-chlorophenoxy)phenyl]-1H-imidazol-4-yl}phenoxy)-propyl]-diethylamine, wherein the method comprises:

a) adding a suitable amount of a volatile solvent to a suitable amount of solid [3-(4-{2-butyl-1-[4-(4-chlorophenoxy)phenyl]-1H-imidazol-4-yl}phenoxy)-propyl]-diethylamine in a vessel;

b) sealing the vessel after step b);

c) maintaining the vessel at room temperature for a sufficient amount of time for the volatile solvent to interact with the solid [3-(4-{2-butyl-1-[4-(4-chlorophenoxy)phenyl]-1H-imidazol-4-yl}phenoxy)-propyl]diethylamine; and d) collecting the solid form from the vessel.

In one embodiment, the volatile solvent in step a) is isopropyl alcohol. In one embodiment, the suitable time in step c) is 5 to 10 days.

One aspect of the present invention is the solid state form Form III of [3-(4-{2-butyl-1-[4-(4-chlorophenoxy)phenyl]-1H-imidazol-4-yl}phenoxy)-propyl]-diethylamine prepared by any of the methods described herein.

In one embodiment, the method involves producing solid state form Form IV of [3-(4-{2-butyl-1-[4-(4-chlorophenoxy)phenyl]-1H-imidazol-4-yl}phenoxy)-propyl]-diethylamine, wherein the method comprises:

a) dissolving a suitable amount of [3-(4-{2-butyl-1-[4-(4-chlorophenoxy)phenyl]-1H-imidazol-4-yl}phenoxy)-propyl]-diethylamine in a suitable amount of a suitable solvent at room temperature to make a solution;

b) stirring the solution from step a);

c) adding a suitable amount of a suitable anti-solvent; and d) collecting the solid product produced from step c).

In one embodiment, the suitable solvent in step a) is toluene. In one embodiment, the suitable anti-solvent in step c) is hexane.

In another embodiment, the method involves producing solid state form Form IV of [3-(4-{2-butyl-1-[4-(4-chlorophenoxy)phenyl]-1H-imidazol-4-yl}phenoxy)-propyl]-diethylamine, wherein the method comprises:

a) slurrying a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at a suitable temperature; and b) collecting the solid produced from step a).

In one embodiment, the suitable solvent system in step a) is selected from the group consisting of toluene, ethyl acetate, anisole, ethyl acetate/hexane, toluene/hexane, and ethanol/hexane. In one embodiment, the suitable temperature is room temperature or 35° C. in step a).

In yet another embodiment, the method involves producing solid state form Form IV of [3-(4-{2-butyl-1-[4-(4-chlorophenoxy)phenyl]-1H-imidazol-4-yl}phenoxy)-propyl]-diethylamine, wherein the method comprises:

a) dissolving a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at room temperature to make a solution;

b) adding a suitable amount of a polymer mixture to the solution from step a) to make a suspension;

c) allowing the suspension of step b) to evaporate at room temperature; and d) collecting the solid produced from step c).

In one embodiment, the suitable solvent system in step a) is isopropyl acetate/hexane. In one embodiment, the polymer mixture in step b) is poly(methyl methacrylate)/sodium alginate/hydroxyethyl cellulose.

In still yet another embodiment, the method involves producing solid state form Form IV of [3-(4-{2-butyl-1-[4-(4-chlorophenoxy)phenyl]-1H-imidazol-4-yl}phenoxy)-propyl]-diethylamine, wherein the comprises:

a) suspending a suitable amount of [3-(4-{2-butyl-1-[4-(4-chlorophenoxy)phenyl]-1H-imidazol-4-yl}phenoxy)-propyl]-diethylamine in a suitable amount of a suitable solvent system at room temperature to make a suspension;

b) heating the suspension from step a) to a suitable temperature and equilibrating for a suitable amount of time;

c) optionally filtering the suspension from step b);

d) slowly cooling to a suitable temperature over a suitable amount of time; and e) collecting the solid produced from step d).

In one embodiment, the suitable solvent system in step a) is dioxane/water. In one embodiment, the suitable temperature is about 40° C. and the suitable amount of time is about 1 hour in step b). In one embodiment, the suitable temperature is about 5° C. and the suitable time is about 5.5 hours in step d). In one embodiment, if no solid is obtained after cooling to about 5° C., a further cooling to −20° C. step is performed. In one embodiment, if no solid is obtained after cooling to about 5° C., an evaporation at room temperature step is performed.

One aspect of the present invention is the solid state form Form IV of [3-(4-{2-butyl-1-[4-(4-chlorophenoxy)phenyl]-1H-imidazol-4-yl}phenoxy)-propyl]-diethylamine prepared by any of the methods described herein.

To ensure no chemical transformation or degradation has occurred, the purity of each polymorph may be confirmed using HPLC and then characterized by its physio-chemical properties such as DSC, X-ray powder diffraction, infrared spectrum, Raman spectrum, and/or solid state $^{13}$C NMR.

In another aspect, the present invention provides mixtures comprising different polymorphs of COMPOUND I. In one embodiment, a mixture comprises a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 5.4°, 21.5°, and 22.0°±0.2° and a second solid state form of [3-(4-{2-butyl-1-[4-(4-chlorophenoxy)phenyl]-1H-imidazol-4-yl}phenoxy)-propyl]-diethylamine, wherein the second solid state form is characterized by an XRPD pattern having peaks at 2θ angles of 18.8° and 20.1°±0.2. In one embodiment, a mixture comprises b) a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 19.7°, 22.0°, and 30.2°±0.2° and a second solid state form of [3-(4-{2-butyl-1-[4-(4-chlorophenoxy)phenyl]-1H-imidazol-4-yl}phenoxy)-propyl]-diethylamine, wherein the second solid state form is characterized by an XRPD pattern having peaks at 2θ angles of 18.8° and 20.1°±0.2. In one embodiment, a mixture comprises a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 5.4°, 21.5°, and 22.0°±0.2° and a second solid state form of [3-(4-{2-butyl-1-[4-(4-chlorophenoxy)phenyl]-1H-imidazol-4-yl}phenoxy)-propyl]-diethylamine, wherein the second solid state form is characterized by an XRPD pattern having peaks at 2θ angles of 16.5° and 26.8°±0.2. In one embodiment, a mixture comprises b) a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 19.7°, 22.0°, and 30.2°±0.2° and a second solid state form of [3-(4-{2-butyl-1-[4-(4-chlorophenoxy)phenyl]-1H-imidazol-4-yl}phenoxy)-propyl]diethylamine, wherein the second solid state form is characterized by an XRPD pattern having peaks at 2θ angles of 16.5° and 26.8°±0.2. In one embodiment, a mixture comprises a crystalline form of [3-(4-{2-butyl-1-[4-(4-chlorophenoxy)phenyl]-1H-imidazol-4-yl}phenoxy)-propyl]-diethylamine, characterized by an XRPD pattern having peaks at 2θ angles of 5.4°, 21.5°, and 22.0°±0.2° and a second solid state form of [3-(4-{2-butyl-1-[4-(4-chlorophenoxy)phenyl]-1H-imidazol-4-yl}phenoxy)-propyl]-diethylamine, wherein the second solid state form is characterized by an XRPD pattern having peaks at 2θ angles of 19.7°, 22.0°, and 30.2°±0.2°. In one embodiment, a mixture comprises two or more of Form I, Form II, Form III, or Form IV of COMPOUND I. In one embodiment, ratio of one solid state form to a second solid state form by weight may be between 9:1 and 1:9, respectively. In an embodiment, the ratio by weight of one solid state form to a second solid state form is 9:1, 8:2, 7:3, 6:4, 5:5, 4:6, 3:7, 2:8, or 1:9.

Pharmaceutical Compositions

In another aspect, the present invention provides pharmaceutical compositions comprising one or more polymorphic forms of COMPOUND I. In one embodiment, a pharmaceutical composition comprises Form III of COMPOUND I and a pharmaceutically acceptable excipient, diluent, carrier, or mixture thereof. In one embodiment, a pharmaceutical composition comprises Form IV of COMPOUND I and a pharmaceutically acceptable excipient, diluent, carrier, or mixture thereof. In one embodiment, a pharmaceutical composition comprises Form III and Form IV of COMPOUND I and a pharmaceutically acceptable excipient, diluent, carrier, or mixture thereof. In one embodiment, a pharmaceutical composition comprises Form I and Form III of COMPOUND I and a pharmaceutically acceptable excipient, diluent, carrier, or mixture thereof. In one embodiment, a pharmaceutical composition comprises Form II and Form III of COMPOUND I and a pharmaceutically acceptable excipient, diluent, carrier, or mixture thereof. In one embodiment, a pharmaceutical composition comprises Form I and Form IV of COMPOUND I and a pharmaceutically acceptable excipient, diluent, carrier, or mixture thereof. In one embodiment, a pharmaceutical composition comprises Form II and Form IV of COMPOUND I and a pharmaceutically acceptable excipient, diluent, carrier, or mixture thereof. In one embodiment, a pharmaceutical composition comprises one or more of Form I, Form II, Form III, or Form IV of COMPOUND I and a pharmaceutically acceptable excipient, diluent, carrier, or mixture thereof.

In another aspect, the present invention also provides methods of producing a pharmaceutical composition comprising one or polymorphs of COMPOUND I. In one embodiment, a method of producing a pharmaceutical composition comprises combining Form III of COMPOUND I with a pharmaceutically acceptable excipient, diluent, carrier, or a mixture thereof. In one embodiment, a method for producing a pharmaceutical composition comprises combining Form IV of COMPOUND I with a pharmaceutically acceptable excipient, diluent, carrier, or a mixture thereof. In one embodiment, a method for producing a pharmaceutical composition comprises combining Form III and Form IV of COMPOUND I with a pharmaceutically acceptable excipient, diluent, carrier, or a mixture thereof. In one embodiment, a method for producing a pharmaceutical composition comprises combining Form III and Form I of COMPOUND I with a pharmaceutically acceptable excipient, diluent, carrier, or a mixture thereof. In one embodiment, a method for producing a pharmaceutical composition comprises combining Form III and Form II of COMPOUND I with a pharmaceutically acceptable excipient, diluent, carrier, or a mixture thereof. In one embodiment, a method for producing a pharmaceutical composition comprises combining Form IV and Form I of COMPOUND I with a pharmaceutically acceptable excipient, diluent, carrier, or a mixture thereof. In one embodiment, a method for producing a pharmaceutical composition comprises combining Form IV and Form II of COMPOUND I with a pharmaceutically acceptable excipient, diluent, carrier, or a mixture thereof. In one embodiment, a method for producing a pharmaceutical composition comprises combining one or more of Form I, Form II, Form III, or Form IV of COMPOUND I and a pharmaceutically acceptable excipient, diluent, carrier, or mixture thereof.

Pharmaceutical compositions of the present invention comprising a Form I, Form II, Form III, Form IV or mixtures thereof of COMPOUND I may be in a form suitable for oral use, for example, as tablets, troches, lozenges, dispersible powders or granules, or hard or soft capsules. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations.

Tablets, tronches, lozenges, dispersible powders or granules, or hard or soft capsules may contain one or more polymorphs of COMPOUND I in admixture with non-toxic pharmaceutically-acceptable excipients which are suitable for the manufacture of such tablets, tronches, lozenges, dispersible powders or granules, or hard or soft capsules. These excipients may be for example, inert diluents, such as calcium carbonate, sodium carbonate, lactose, microcrystalline cellulose, calcium phosphate or sodium phosphate; granulating and disintegrating agents, for example corn starch, croscarmelose sodium, or alginic acid; binding agents, for example, starch, gelatin or acacia; and lubricating agents or glidants, for example magnesium stearate, stearic acid, colloidal silicon dioxide, or talc. Hard gelatin capsules may include one or more polymorphs of COMPOUND I in combination with an inert solid excipient, diluent, carrier, or mixture thereof.

A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation, the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art.

Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa. 1985, the contents of which are incorporated herein by reference.

Methods of Treatment

In another embodiment, the present invention also provides pharmaceutical compositions comprising a therapeutically effective amount of COMPOUND I wherein a therapeutically effective amount of COMPOUND I comprises a sufficient amount for the treatment of a RAGE mediated disorder. In another embodiment, a pharmaceutical composition may comprise a therapeutically effective amount of Form I of COMPOUND I. In another embodiment, a pharmaceutical composition may comprise a therapeutically effective amount of Form II of COMPOUND I. In another embodiment, a pharmaceutical composition may comprise a therapeutically effective amount of Form III of COMPOUND I. In another embodiment, a pharmaceutical composition may comprise a therapeutically effective amount of Form IV of COMPOUND I. In another embodiment, a pharmaceutical composition may comprise a therapeutically effective amount of a mixture of one or more of Form I, II, III, or IV of COMPOUND I.

In another aspect, the present invention provides a method for treating a RAGE mediated disease comprising administering one or more polymorphic forms of COMPOUND I to a subject in need thereof. The method may comprise administering a pharmaceutical composition comprising a therapeutically effective amount of COMPOUND I to a subject in need thereof.

A pharmaceutical composition of the present invention may be administered at a dosage level of less than 100 mg of compound per day. In another embodiment, the dosage level of administration is greater than 1 mg of compound per day. The amount of active ingredient that may be combined with the carrier materials to produce a single dosage will vary depending upon the host treated and the particular mode of administration. For example, in one non-limiting embodiment, a dosage unit forms, such as a tablet or capsule, intended for oral administration to humans may contain less than 100 mg of COMPOUND I with an appropriate and convenient amount of carrier material. In another embodiment, the dosage level of administration is greater than 1 mg of compound per day. In another embodiment, the dosage level of administration is 5, 10 or 20 mg of compound per day.

The dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination and the severity of the particular disease undergoing therapy.

EXAMPLES

Analytical Methods Used to Characterize Forms I and II

Methods used to collect XRPD, solid state $^{13}C$ NMR, FT-IR, Raman, TGA, and DSC data for Forms I and II of COMPOUND I are provided in U.S. Pat. No. 7,884,219.

Analytical Methods Used to Characterize Forms III and IV

X-ray Powder Diffraction (XRPD) Analysis

XRPD analysis was performed with a Panalytical X'Pert[3] Powder XRPD on a Si zero-background holder. The 2θ position was calibrated against Panalytical Si reference standard disc. The XRPD parameters used are listed in Table 1.

TABLE 1

| Parameters for XRPD test | |
|---|---|
| Parameters | Reflection Mode |
| X-Ray wavelength | Cu, kα |
| Kα1 (Å) | 1.540598 |
| Kα2 (Å) | 1.544426 |
| Kα2/Kα1 intensity ratio | 0.50 |
| X-Ray tube setting | 45 kV, 40 mA |
| Divergence slit | Fixed ⅛° |
| Scan mode | Continuous |
| Scan range | (° 2TH)3-40 |
| Scan step time [s] | 18.87 |
| Step size (° 2TH) | 0.0131 |
| Test Time | 4 min 15 s |

Thermogravimetry Analysis (TGA) and Differential Scanning Calorimetry (DSC)

TGA data were collected using a TA Q500 and Q550 from TA Instruments. DSC was performed using a TA Q2000 from TA Instruments. DSC was calibrated with Indium reference standard and the TGA was calibrated using nickel reference standard. Detailed parameters used are listed in Table 2.

TABLE 2

| Parameters for TGA and DSC test | | |
|---|---|---|
| Parameters | TGA | DSC |
| Method | Ramp | Ramp |
| Sample pan | Aluminum, open | Aluminum, crimped |
| Temperature | RT - desired temperature | 25° C. - desired temperature |
| Heating rate | 10° C./min | 10° C./min |
| Purge gas | $N_2$ | $N_2$ |

Crystalline Form II was used as the starting material in each of the following Examples.

Example 1

Solid vapor diffusion experiments were conducted using 16 different solvents. Approximate 30 mg of starting material was weighed into a 3-mL vial, which was placed into a 20-mL vial with 2 mL of volatile solvent. The 20-mL vial was sealed with a cap and kept at RT for 7 days allowing solvent vapor to interact with sample. The solids were tested by XRPD and the results summarized in Table 3 showed that Type II, gel or mixture of forms were generated.

TABLE 3

| Summary of solid vapor diffusion experiments | |
|---|---|
| Solvent | Solid Form |
| $H_2O$ | Form II |
| Ethanol | Form II |
| Isopropanol | Forms II + III |
| Acetone | Form II |

TABLE 3-continued

Summary of solid vapor diffusion experiments

| Solvent | Solid Form |
|---|---|
| 4-Methyl-2-pentanone | Form II |
| Ethyl acetate | Form II |
| Isopropyl Acetate | Form II |
| Methyl tert-butyl ether | Form II |
| Tetrahydrofuran | Gel |
| Dichloromethane | Form II |
| Toluene | Form II |
| Acetonitrile | Form II |
| Cyclopentyl methyl ether | Form II |
| 2-Methyltetrahydrofuran | Form II |
| $CH_3COOH$ | Gel |
| $CHCl_3$ | Gel |

Example 2

Slow evaporation experiments were performed under six conditions. Briefly, 30 mg of starting material was dissolved in 1-6 mL of solvent in a 20-mL glass vial. If no dissolution was achieved, suspensions were filtered using a PTFE (pore size of 0.2 μm) and the filtrates were used for the following steps. The visually clear solutions were covered by Parafilm® with 5-10 pinholes and subjected to evaporation at RT. The solids were isolated for XRPD analysis. The results summarized in Table 4 indicated that Type II, gel or mixture of forms were obtained.

TABLE 4

Summary of slow evaporation experiments

| Solvent (v:v) | Solid Form | Solvent (v:v) | Solid Form |
|---|---|---|---|
| 2-Methyltetra-hydrofuran | Form III | Methyl ethyl ketone | Form II |
| Acetic acid | Gel | Methanol | Gel |
| Acetone | Form II | Methyl tert-butyl ether | Form II |
| Acetonitrile | Form II | N-Methyl-2-pyrrolidone⁺ | Gel |
| $CHCl_3$ | Form II | Tetrahydrofuran | Forms II + III |
| Cyclohexane | Form II | Toluene | Gel |
| Dichloromethane | Form II | Acetone/$H_2O$ | — |
| Dioxane | Gel | Methanol/$H_2O$ | Form II |
| Dimethylacetamide* | Gel | Ethanol/$H_2O$ | Gel |
| Ethyl acetate | Form II | Isopropyl alcohol/$H_2O$ | Gel |
| Ethanol | Form II | Tetrahydro-furan/$H_2O$ | Gel |
| Isopropyl alcohol | Form II | Dioxane/$H_2O$ | Form II |
| Isopropyl Acetate | Form II | Acetonitrile/$H_2O$ | Gel |

*Solid was obtained via vacuumed evaporation at RT.
⁺Gel was obtained via vacuumed evaporation at 40° C.
—: Limited solid for XRPD test.

Example 3

A total of 42 anti-solvent addition experiments were carried out. About 30 mg of starting material was dissolved in 0.2-2.0 mL solvent to obtain a clear solution. The solution was magnetically stirred followed by addition of 0.2 mL anti-solvent stepwise till precipitate appeared or the total amount of anti-solvent reached 15.0 mL. The obtained precipitate was isolated for XRPD analysis. Results in Table 5 showed that Types I, II, gel or mixture of forms were obtained.

TABLE 5

Summary of anti-solvent addition experiments

| Solvent | Anti-solvent | Solid Form |
|---|---|---|
| Ethanol | $H_2O$ | Form III |
| Ethanol | n-Heptane | Gel |
| Ethanol | Hexane | Forms II + III |
| n-Propyl alcohol | $H_2O$ | Form II |
| n-Propyl alcohol | n-Heptane | Form II |
| n-Propyl alcohol | Hexane | Forms II + III |
| Isopropyl alcohol | $H_2O$ | Form II |
| Isopropyl alcohol | n-Heptane | Forms II + III |
| Isopropyl alcohol | Hexane | Forms II + III |
| Tetrahydrofuran | $H_2O$ | Form III |
| Tetrahydrofuran | n-Heptane | Form II |
| Tetrahydrofuran | Hexane | Form II |
| Acetone | $H_2O$ | Form II |
| Acetone | n-Heptane | Form II |
| Acetone | Hexane | Form II |
| 2-Methyltetrahydrofuran | $H_2O$ | Form II |
| 2-Methyltetrahydrofuran | n-Heptane | Form II |
| 2-Methyltetrahydrofuran | Hexane | Form II |
| Dioxane | $H_2O$ | Forms II + III |
| Dioxane | n-Heptane | Form II |
| Dioxane | Hexane | Form II |
| Methanol | $H_2O$ | Form II |
| Acetonitrile | $H_2O$ | Form II |
| N-Methyl-2-pyrrolidone | $H_2O$ | Form II |
| Dimethylacetamide | $H_2O$ | Form II |
| Dimethyl sulfoxide | $H_2O$ | Low crystallinity |
| Ethyl acetate | n-Heptane | Form II |
| Ethyl acetate | Hexane | Form II |
| Isopropyl Acetate | n-Heptane | Form II |
| Isopropyl Acetate | Hexane | Forms II + III |
| Methyl tert-butyl ether | n-Heptane | Form II |
| Methyl tert-butyl ether | Hexane | Form II |
| Methyl ethyl ketone | n-Heptane | Form II |
| Methyl ethyl ketone | Hexane | Form III |
| $CH_2Cl_2$ | n-Heptane | Form II |
| $CH_2Cl_2$ | Hexane | Form II |
| $CHCl_3$ | n-Heptane | Form II |
| $CHCl_3$ | Hexane | Form II |
| Toluene | n-Heptane | Form II |
| Toluene | Hexane | Forms II + IV |
| Cyclopentyl methyl ether | n-Heptane | Form II |
| Cyclopentyl methyl ether | Hexane | Form II |

No solid was obtained in all solvent systems with n-Heptane and Hexane, so the solids were obtained via evaporation at RT.

Example 4

Slurry experiments were conducted at RT in different solvent systems. About 30 mg of starting material was suspended in 0.1~0.2 mL of solvent in a 3-mL glass vial. After the suspension was stirred magnetically for 7 days at RT, the remaining solids were isolated for XRPD analysis. Results summarized in Table 6 indicated that Type II, III, IV, or mixture of forms were obtained.

TABLE 6

Summary of slurry conversion experiments at RT

| Solvent (v:v) | Solid Form |
|---|---|
| Isopropyl alcohol | Form III |
| Ethanol | Form III |
| Acetonitrile | Form II |
| Toluene | Form IV |
| Cyclohexane | Form II |
| n-Heptane | Form II |
| Hexane | Form II |
| Ethyl Acetate | Forms III + IV |

TABLE 6-continued

Summary of slurry conversion experiments at RT

| Solvent (v:v) | Solid Form |
|---|---|
| Cyclopentyl methyl ether | Form III |
| Acetone | Form III |
| Anisole | Form IV |
| $H_2O$ | Form II |
| Ethanol/$H_2O$ (0.97/0.03, $a_w$ = 0.2) | Form III |
| Ethanol/$H_2O$ (0.927/0.073, $a_w$ = 0.4) | Form III |
| Ethanol/$H_2O$ (0.855/0.145, $a_w$ = 0.6) | Low crystallinity |
| Ethanol/$H_2O$ (0.704/0.296, $a_w$ = 0.8) | Low crystallinity |
| N-propyl alcohol/n-Heptane (1:3) | Form III |
| Ethanol/Hexane (1:3) | Form III |
| Methyl ethyl ketone/Hexane (1:3) | Form III |
| 4-Methyl-2-pentanone/Hexane (1:3) | Forms II + III |
| Isopropyl alcohol/Hexane (1:3) | Form III |
| $CHCl_3$/Hexane (1:3) | Form II |
| Anisole/Hexane(1:3) | Form II |
| Methyl tert-butyl ether/Hexane (1:3) | Form II |
| Acetone/Hexane (1:3) | Form II |
| Ethyl acetate/Hexane (1:3) | Forms III + IV |
| Isopropyl acetate/Hexane (1:3) | Form II |
| Toluene/Hexane(1:3) | Form IV |
| 2-Methyltetrahydrofuran/Hexane (1:3) | Forms II + III |
| Dioxane/Hexane (1:3) | Form III |

Example 5

Slurry experiments were also conducted at 35° C. in different solvent systems. About 30 mg of starting material was suspended in 0.1-0.3 mL of solvent in a 3 mL glass vial. After the suspension was stirred for about 7 days at 35° C., the remaining solids were isolated for XRPD analysis. Results summarized in Table 7 indicated that Form II, III, IV, or mixture of forms were obtained.

TABLE 7

Summary of slurry conversion experiments at 35° C.

| Solvent | Solid Form |
|---|---|
| Isopropyl alcohol | Forms II + III |
| Ethanol | Forms II + III |
| Acetonitrile[#] | Form II |
| Toluene | Form IV |
| Cyclohexane | Form III |
| Heptane | Form II |
| Hexane | Form II |
| Ethyl acetate | Form III |
| Cyclopentyl methyl ether | Forms II + III |
| Acetone | Forms II + III |
| Anisole* | Forms III + IV |
| $H_2O$ | Form II |
| Ethanol/$H_2O$ (0.97/0.03, $a_w$ = 0.2)* | Form III |
| Ethanol/$H_2O$ (0.927/0.073, $a_w$ = 0.4)* | Form III |
| Ethanol/$H_2O$ (0.855/0.145, $a_w$ = 0.6)[#] | Form III |
| Ethanol/$H_2O$ (0.704/0.296, $a_w$ = 0.8)* | Form III |
| N-propyl alcohol/Heptane (1:6)* | Form III |
| Ethanol/Hexane (1:6)* | Forms III + IV |
| Methyl ethyl ketone/Hexane (1:6) | Forms II + III |
| 4-Methyl-2-pentanone/Hexane (1:6) | Forms II + III |
| Isopropyl alcohol/Hexane (1:6) | Forms II + III |
| $CHCl_3$/Hexane (1:6) | Form II |
| Anisole/Hexane(1:6)* | Forms II + III |
| Methyl tert-butyl ether/Hexane (1:6) | Forms II + III |
| Acetone/Hexane (1:6) | Form II |
| Ethyl acetate/Hexane (1:6) | Forms II + III |
| Isopropyl acetate/Hexane (1:6) | Forms II + III |
| Toluene/Hexane(1:6)* | Form III |
| 2-Methyltetrahydrofuran/Hexane (1:6) | Forms II + III |
| Dioxane/Hexane (1:6) | Forms II + III |

Up to 150 mg starting material were added to prepare suspension due to the large solubility at 35° C.
*, [#]After adding 150 mg starting material the solution was clear.
*Solid precipitated when the sample was removed from hot plate to RT.
[#]Solid precipitated when the sample was removed from hot plate to 5° C.

Example 6

Polymer-induced crystallization experiments were also conducted at 30 conditions with two polymer mixtures. About 30 mg of starting material was dissolved in 1~2 mL of solvent in a 3 mL glass vial. If no dissolution was achieved, suspensions were filtered using a PTFE (pore size of 0.2 μm) and the filtrates were used for the following steps. About 2 mg of polymer mixture added into clear solutions. Suspensions were covered by Parafilm® with 5~10 pinholes and subjected to evaporation at RT. The solids were isolated for XRPD analysis. Results summarized in Table 8 indicated that Type II, III, gel or mixture of forms were obtained.

TABLE 8

Summary of polymer-induced crystallization experiments

| Solvent | Polymer Mixture | Solid Form |
|---|---|---|
| Isopropyl alcohol | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form III |
| Ethanol | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form II |
| Acetonitrile | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form II |
| Toluene | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form II |
| Cyclohexane | polyvinyl pyrrolidone (PVP), polyvinyl alcohol (PVA), polyvinylchloride (PVC), hypromellose (HPMC), methyl cellulose (MC) (mass ratio of 1:1:1:1:1) | Forms II + III |
| Ethyl acetate/hexane | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form III |
| Acetone/hexane | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form III |

TABLE 8-continued

Summary of polymer-induced crystallization experiments

| Solvent | Polymer Mixture | Solid Form |
|---|---|---|
| Tetrahydrofuran/hexane | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form II |
| Methanol/H$_2$O | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form II |
| Ethanol/H$_2$O | polyvinyl pyrrolidone (PVP), polyvinyl alcohol (PVA), polyvinylchloride (PVC), hypromellose (HPMC), methyl cellulose (MC) (mass ratio of 1:1:1:1:1) | Form II |
| Isopropyl alcohol | poly(methyl methacrylate) (PMMA) sodium alginate (SA), and hydroxyethyl cellulose (HEC) (mass ratio of 1:1:1) | Forms II + III |
| Ethanol | poly(methyl methacrylate) (PMMA) sodium alginate (SA), and hydroxyethyl cellulose (HEC) (mass ratio of 1:1:1) | Gel |
| Acetonitrile | poly(methyl methacrylate) (PMMA) sodium alginate (SA), and hydroxyethyl cellulose (HEC) (mass ratio of 1:1:1) | Form II |
| Toluene | poly(methyl methacrylate) (PMMA) sodium alginate (SA), and hydroxyethyl cellulose (HEC) (mass ratio of 1:1:1) | Gel |
| Cyclohexane | poly(methyl methacrylate) (PMMA) sodium alginate (SA), and hydroxyethyl cellulose (HEC) (mass ratio of 1:1:1) | Form II |
| Isopropyl acetate/hexane | poly(methyl methacrylate) (PMMA) sodium alginate (SA), and hydroxyethyl cellulose (HEC) (mass ratio of 1:1:1) | Forms III + IV |
| Methyl ethyl ketone/hexane | poly(methyl methacrylate) (PMMA) sodium alginate (SA), and hydroxyethyl cellulose (HEC) (mass ratio of 1:1:1) | Form III |
| Dioxane/hexane | poly(methyl methacrylate) (PMMA) sodium alginate (SA), and hydroxyethyl cellulose (HEC) (mass ratio of 1:1:1) | Gel |
| Isopropyl alcohol/H$_2$O | poly(methyl methacrylate) (PMMA) sodium alginate (SA), and hydroxyethyl cellulose (HEC) (mass ratio of 1:1:1) | Form II |
| N-propyl alcohol/H$_2$O | poly(methyl methacrylate) (PMMA) sodium alginate (SA), and hydroxyethyl cellulose (HEC) (mass ratio of 1:1:1) | Forms II + III |

Example 7

Fifteen liquid vapor diffusion experiments were conducted. Approximate 30 mg of starting material was dissolved in appropriate solvent to obtain a clear solution in a 3-mL vial. This solution was then placed into a 20-mL vial with 3 mL of volatile solvents. The 20-mL vial was sealed with a cap and kept at RT allowing sufficient time for organic vapor to interact with the solution. The precipitates were isolated for XRPD analysis. The results summarized in Table 9 showed that Form II or mixture of forms was generated.

TABLE 9

Summary of liquid vapor diffusion experiments

| Solvent | Anti-solvent | Solid Form |
|---|---|---|
| 2-Methyltetrahydrofuran* | Hexane | Form II |
| Acetone* | n-heptane | Form II |
| CHCl$_3$* | n-heptane | Form II |
| Cyclohexane* | n-heptane | Form II |
| Dichloromethane* | Hexane | Form II |
| Ethyl acetate* | Hexane | Form II |
| Ethanol* | Hexane | Form II |
| Isopropyl alcohol* | Hexane | Form II |
| Isopropyl acetate* | n-heptane | Form II |
| Methyl ethyl ketone* | Hexane | Forms II + III |
| 4-Methyl-2-pentanone* | n-heptane | Form II |
| Methyl tert-butyl ether | Hexane | Form II |
| N-propyl alcohol* | n-heptane | Form II |
| Tetrahydrofuran | n-heptane | Form II |
| Toluene* | n-heptane | Form II |

*Solids were obtained via evaporation at RT.

Example 8

Slow cooling experiments were conducted in 25 solvent systems. About 50-100 mg of starting material was suspended in 0.3-0.4 mL of solvent in a 4-mL glass vial at RT. The suspension was then heated to 40° C., equilibrated for one hour and filtered using a PTFE membrane (pore size of 0.20 µm). For the systems which were still clear solution, filtration skipped. Filtrates were slowly cooled down to 5° C. within 5.5 hrs. For the systems which no solid obtained either cooling to −20° C. or evaporation at RT were employed. Results summarized in Table 10 indicated Form II, Form III, Form IV or mixture of forms were observed.

TABLE 10

Summary of slow cooling experiments

| Solvent (v:v) | Solid Form |
|---|---|
| Isopropyl alcohol* | Form III |
| Ethanol | Form II |
| Acetonitrile* | Form III |
| Cyclohexane | Form III |
| n-Butanol* | Form III |
| Ethanol/n-Heptane (1:6) | Form III |
| Methyl ethyl ketone/n-Heptane (1:6)* | Form III |
| CHCl$_3$/n-Heptane* | Form II |
| Isopropyl alcohol/n-Heptane (1:6)* | Form III |
| Methyl tert-butyl ether/n-heptane (1:6)* | Forms II + III |
| Acetone/n-Heptane (1:6) | Form II |
| CHCl$_3$/n-Hexane (1:6)* | Form III |
| Isopropyl alcohol/Hexane(1:6) | Form III |
| Methyl tert-butyl ether/Hexane (1:6) | Form III |
| Ethyl acetate/Hexane (1:6) | Form III |
| Isopropyl acetate/Hexane (1:6) | Form II |
| Toluene/Hexane(1:6)* | Forms II + III |
| Cyclopentyl methyl ether/Hexane (1:6)* | Form III |
| Acetonitrile/H$_2$O (1:2)+ | Gel |
| Acetone/H$_2$O (1:2)+ | — |
| Tetrahydrofuran/H$_2$O (1:2)+ | Gel |
| 2-Methyltetrahydrofuran/H$_2$O (1:6)+ | Form II |
| Dioxane/H$_2$O (1:2)+ | Form III |

TABLE 10-continued

Summary of slow cooling experiments

| Solvent (v:v) | Solid Form |
|---|---|
| Dimethylacetamide/H$_2$O (1:2)⁺ | Gel |
| n-Propyl alcohol/H$_2$O (1:2)⁺ | Gel |

The first 18 solutions were still clear after adding about 100 mg starting material, filtration skipped.
*Solids were obtained via cooling to −20° C.
⁺Solids were obtained via evaporation at RT
—: No solid precipitated Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the present invention.

The invention claimed is:

1. A solid state form of [3-(4-{2-butyl-1-[4-(4-chlorophenoxy)phenyl]-1H-imidazol-4-yl}phenoxy)-propyl]-diethylamine, wherein the solid state form is crystalline and is characterized by an X-ray Powder Diffraction (XRPD) pattern having peaks at 2θ angles of 5.4°±0.2°, 21.5°±0.2°, and 22.0°±0.2°.

2. The solid state form of claim 1, characterized by an XRPD pattern as shown in FIG. 1.

3. The solid state form of claim 2, characterized by an endothermic peak at about 59° C., as determined by Differential Scanning Calorimetry (DSC).

4. The solid state form of claim 2, characterized by a Differential Scanning Calorimetry (DSC) profile as shown in FIG. 2.

5. The solid state form of claim 2, characterized by an about 2.3 wt % loss between room temperature and about 150° C., as determined by Thermogravimetry Analysis (TGA).

6. The solid state form of claim 2, characterized by a Thermogravimetry Analysis (TGA) profile as shown in FIG. 2.

7. The solid state form of claim 1, characterized by the following features:
i) an XRPD pattern having peaks at 2θ angles of 5.4°±0.2°, 21.5°±0.2°, and 22.0°±0.2°;
ii) a Differential Scanning Calorimetry (DSC) profile as shown in FIG. 2; and
iii) a Thermogravimetry Analysis (TGA) profile as shown in FIG. 2.

8. A solid state form of [3-(4-{2-butyl-1-[4-(4-chlorophenoxy)phenyl]-1H-imidazol-4-yl}phenoxy)-propyl]-diethylamine, wherein the solid state form is crystalline and is characterized by an X-ray Powder Diffraction (XRPD) pattern having peaks at 2θ angles of 19.7°±0.2°, 22.0°±0.2°, and 30.2°±0.2°.

9. The solid state form of claim 8, characterized by an XRPD pattern having peaks at 2θ angles of 5.4°±0.2°, 19.7°±0.2°, 21.8°±0.2°, 22.0°±0.2°, and 30.2°±0.2°.

10. The solid state form of claim 8, characterized by an XRPD pattern as shown in FIG. 3.

11. The solid state form of claim 8, characterized by an endothermic peak at about 51.9° C., as determined by Differential Scanning Calorimetry (DSC).

12. The solid state form of claim 8, characterized by a Differential Scanning Calorimetry (DSC) profile as shown in FIG. 4.

13. The solid state form of claim 8, characterized by an about 4.2 wt % loss between room temperature and about 150° C., as determined by Thermogravimetry Analysis (TGA).

14. The solid state form of claim 8, characterized by a TGA profile as shown in FIG. 4.

15. The solid state form of claim 8, characterized by the following features:
i) an XRPD pattern having peaks at 2θ angles of 19.7°±0.2°, 22.0°±0.2°, and 30.2°±0.2°;
ii) a Differential Scanning Calorimetry (DSC) profile as shown in FIG. 4; and
iii) a TGA profile as shown in FIG. 4.

16. A pharmaceutical composition comprising the solid state form of claim 1 and one or more pharmaceutically acceptable carriers or diluents.

17. A pharmaceutical composition comprising the solid state form of claim 8 and one or more pharmaceutically acceptable carriers or diluents.

* * * * *